US012558249B2

(12) United States Patent
Eyal et al.

(10) Patent No.: US 12,558,249 B2
(45) Date of Patent: Feb. 24, 2026

(54) CRANIAL ORTHOSIS AND METHOD THEREFOR

(71) Applicant: OCCIPO Ltd., Sde-Ilan (IL)

(72) Inventors: Shai Eyal, Sde-Ilan (IL); Naama Eyal, Sde-Ilan (IL); Jonathan Bar-Or, Pardes Hanna (IL)

(73) Assignee: OCCIPO Ltd., Sde-Ilan (IL)

( * ) Notice: Subject to any disclaimer, the term of this patent is extended or adjusted under 35 U.S.C. 154(b) by 0 days.

(21) Appl. No.: 18/609,700

(22) Filed: Mar. 19, 2024

(65) Prior Publication Data

US 2024/0350293 A1 Oct. 24, 2024

Related U.S. Application Data

(63) Continuation-in-part of application No. PCT/IL2022/051000, filed on Sep. 19, 2022.

(30) Foreign Application Priority Data

Sep. 19, 2021 (IL) .......................................... 286516

(51) Int. Cl.
*A61F 5/058* (2006.01)
(52) U.S. Cl.
CPC ................................ *A61F 5/05891* (2013.01)
(58) Field of Classification Search
CPC .... A61F 5/05891; A61F 5/01; A61F 5/05883; A61F 5/058; A61F 5/05; A61F 5/04;
(Continued)

(56) References Cited

U.S. PATENT DOCUMENTS

| 5,094,229 A | 3/1992 | Pomatto et al. |
| 5,425,378 A | 6/1995 | Swezey et al. |

(Continued)

FOREIGN PATENT DOCUMENTS

| CN | 106236349 | 12/2016 |
| CN | 109172080 | 1/2019 |
| KR | 100826858 B1 * | 5/2008 | ......... A61F 5/05891 |

OTHER PUBLICATIONS

PCT International Search Report (mailed Nov. 24, 2022) and Written Opinion (mailed Dec. 1, 2022) for corresponding PCT Application No. PCT/IL2022/051000, 9 pages.
(Continued)

*Primary Examiner* — Tarla R Patel
(74) *Attorney, Agent, or Firm* — Dority & Manning, P.A.

(57) ABSTRACT

A cranial orthosis configured to induce cranial remodeling to achieve symmetry of the skull, as well as adequate proportions between the head width and length, for infants suffering from positional skull deformities comprises a headpiece adapted to encircle, and to be secured to, the skull of an infant suffering from positional skull deformity in such a way that contact between a flattened occipital area of the infant and a flat surface on top of which the infant is lying is prevented so that unrestricted occipital growth (or other places) is able to be induced, wherein said headpiece is adjustable to take into account cranial growth of the infant and to redirect the head growth. The headpiece is capable of adjusting the infant's head growth, to improve symmetry and obtain adequate proportions.

17 Claims, 39 Drawing Sheets

(58) Field of Classification Search

CPC ............... A61F 5/00; A61F 2007/0002; A61F 2007/0007; A61F 2007/0012; A61F 5/3707

See application file for complete search history.

(56) References Cited

U.S. PATENT DOCUMENTS

| | | | |
|---|---|---|---|
| 6,423,019 | B1 | 7/2002 | Papay et al. |
| 6,428,494 | B1 | 8/2002 | Schwenn et al. |
| 8,827,939 | B2 | 9/2014 | Slatten |
| 8,864,665 | B2 | 10/2014 | Rotondo et al. |
| 9,173,763 | B2 * | 11/2015 | Gilmer ................ A61F 5/05891 |
| 9,980,848 | B2 | 5/2018 | Gilmer et al. |
| 10,682,846 | B2 | 6/2020 | Littlefield et al. |
| 10,695,211 | B2 | 6/2020 | Mottram et al. |
| 2011/0132379 | A1 | 6/2011 | Lee |
| 2013/0289459 | A1 | 10/2013 | Bernardoni |
| 2024/0189576 | A1 * | 6/2024 | Dar ...................... A61B 5/6803 |

OTHER PUBLICATIONS

Cabrera-Martos, et al., "Impact of Torticollis Associated With Plagiocephaly on Infants' Motor Development", The Journal of Craniofacial Surgery, vol. 26, No. 1, Jan. 2015, 6 pages.

Di Rocco et al., "Prevalence and severity of positional plagiocephaly in children and adolescents", Acta Neurochirurgica, vol. 161, No. 6, 2019, 4 pages.

Rogers, "Deformational Plagiocephaly, Brachycephaly, and Scaphocephaly. Part I: Terminology, Diagnosis, and Etiopathogenesis", The Journal of Craniofacial Surgery, vol. 22, No. 1, Jan. 2011, 8 pages.

Supplementary Partial European Search Report received in corresponding Application No. EP 22869545, dated Jun. 24, 2025, 3 pages.

Extended European Search Report received in corresponding Application No. EP 22869545.8, dated Nov. 13, 2025, 11 pages.

* cited by examiner

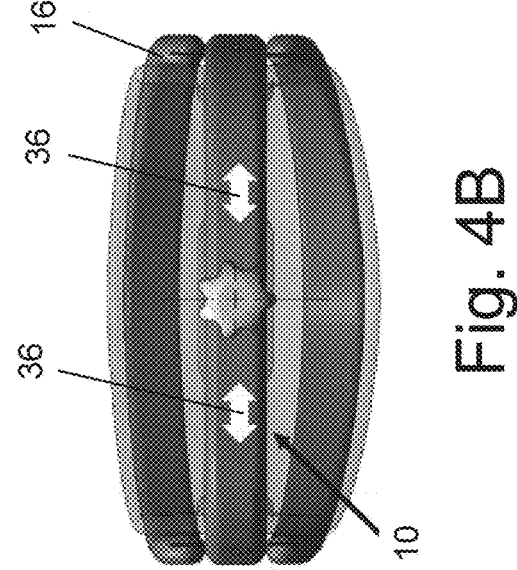
Fig. 4B
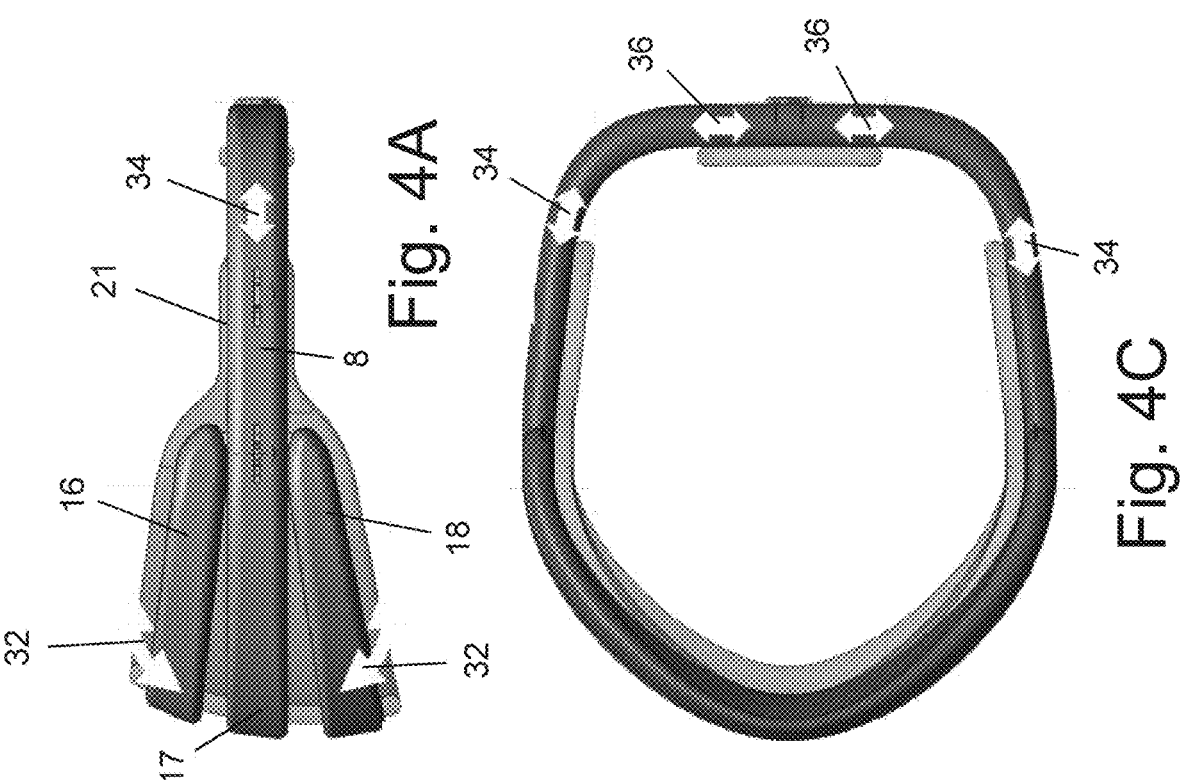
Fig. 4A
Fig. 4C

35

71

72

73

74

114

114

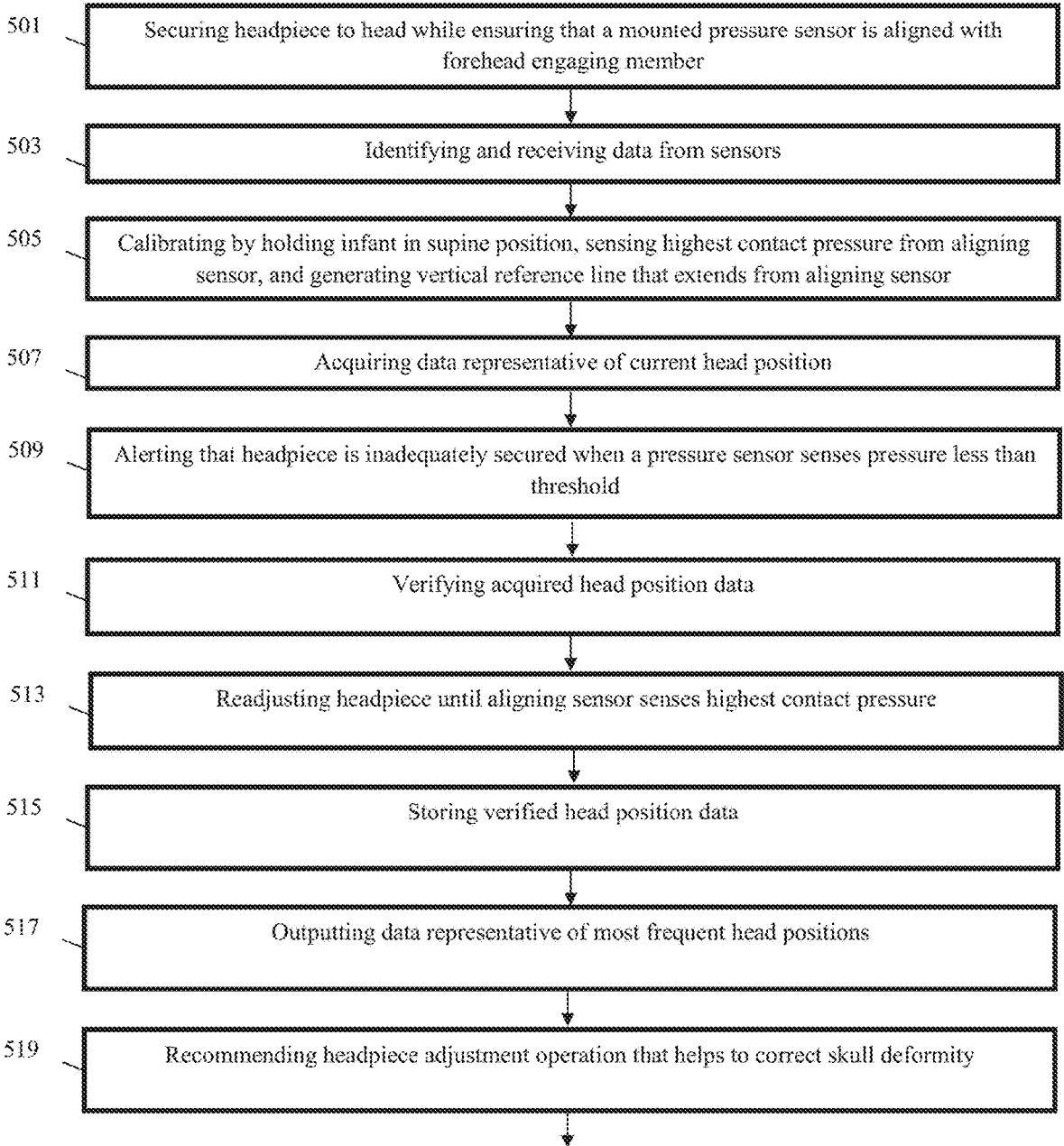

501 — Securing headpiece to head while ensuring that a mounted pressure sensor is aligned with forehead engaging member 503 — Identifying and receiving data from sensors 505 — Calibrating by holding infant in supine position, sensing highest contact pressure from aligning sensor, and generating vertical reference line that extends from aligning sensor 507 — Acquiring data representative of current head position 509 — Alerting that headpiece is inadequately secured when a pressure sensor senses pressure less than threshold 511 — Verifying acquired head position data 513 — Readjusting headpiece until aligning sensor senses highest contact pressure 515 — Storing verified head position data 517 — Outputting data representative of most frequent head positions 519 — Recommending headpiece adjustment operation that helps to correct skull deformity

Fig. 27

CRANIAL ORTHOSIS AND METHOD THEREFOR

CROSS-REFERENCE TO RELATED APPLICATIONS

This application is a continuation-in-part of International Application No. PCT/IL2022/051000, filed on Sep. 19, 2022, which, in turn, claims priority to Israeli Patent Application No. 286516, filed on Sep. 19, 2021, both of which are hereby incorporated herein by reference in their entireties for all purposes.

FIELD OF THE INVENTION

The present invention relates to the field of medical devices for treating deformed skeletal parts. More particularly, the invention relates to a cranial orthosis and an apparatus for monitoring torticollis and cervical muscle imbalance.

BACKGROUND OF THE INVENTION

Positional Skull Deformity (also known as flat head syndrome) is a common condition in infants characterized by asymmetrical or symmetrical posterior occipital flattening. The infant's head is soft and malleable in the first months of life and is therefore susceptible to deformation due to external mechanical pressure. In more severe cases, asymmetry appears in additional cranial areas, which affects also the facial structure (Gary F. Rogers: "Deformational Plagiocephaly, Brachycephaly, and Scaphocephaly", Part I: Terminology, Diagnosis, and Etiopathogenesis). The most common skull deformities are plagiocephaly, brachycephaly and scaphocephaly.

Congenital Muscular Torticollis (CMT) is a postural deformity evident shortly after birth, typically characterized by lateral flexion/side bending of the head to one side and cervical rotation/head turning to the opposite side due to unilateral shortening or imbalance of the sternocleidomastoid muscle. Torticollis is often associated with plagiocephaly (Cabrera-Martos et al.: "Impact of Torticollis Associated with Plagiocephaly on Infants' Motor Development", the Journal of Craniofacial Surgery: January 2015—Volume 26—Issue 1—p 151-156).

The prevalence of plagiocephaly has increased significantly since 1992, due to the American Academy of Pediatrics (AAP) recommendation to lay infants in a supine sleeping position, in order to reduce Sudden Infant Death Syndrome (SIDS). In recent years, the reported rate of plagiocephaly for infants aged up to a year is 16-48%.

The presence of plagiocephaly is statistically associated with a variety of delayed developments (which may be cognitive, motor and linguistic developments), that should be treated. Also, plagiocephaly has substantial esthetic implications regarding the skull structure and facial features. Such implications exist not only in the early years, but also during adolescence (Di Rocco et al.: "Prevalence and severity of positional plagiocephaly in children and adolescents", Acta Neurochirurgica volume 161, pages 1095-1098 (2019). Sometimes, plagiocephaly lapses during the early years and sometimes remains until adolescents.

It is an object of the present invention to provide a cranial orthosis that is suitable to treat plagiocephaly, brachycephaly, and scaphocephaly, and to minimize discomfort to the infants and their families.

It is an additional object of the present invention to provide a cranial orthosis that is cost effective.

It is an additional object of the present invention to provide a cranial orthosis device that is suitable to assist in diagnosing and treating torticollis, and other impairments related to head control and head movements.

Other objects and advantages of the invention will become apparent as the description proceeds.

SUMMARY OF THE INVENTION

An adjustable cranial orthosis configured to induce cranial remodeling to achieve skull symmetry and desired proportions for infants suffering from positional skull deformities comprises a headpiece capable of encircling, and being secured to, the skull of an infant suffering from positional plagiocephaly, brachycephaly or scaphocephaly in such a way that contact between a flattened occipital area of the infant and a flat surface on top of which the infant is lying is prevented so that unrestricted occipital growth is able to be induced, and also in such a way, the device gently restricts the growth of the head in prominent areas, wherein said headpiece comprises separate posterior and anterior sections that are capable of being coupled together, a widthwise adjustment mechanism operatively connected to the anterior section, and at least one lengthwise adjustment mechanism operatively connected to the posterior section, and wherein the widthwise adjustment mechanism and the at least one lengthwise adjustment mechanism are operable to suitably adjust the headpiece to take into account cranial growth of the infant and to redirect the head growth.

In one aspect, the posterior and anterior sections are semi rigid, flexible or rigid.

In one aspect, the posterior section is configured with one or more arcuate pieces that follow a contour of a symmetric skull.

In one aspect, the headpiece further comprises a padding member attached to an inner face of the one or more arcuate pieces, allowing the infant's head to rest in a concave space defined by the one or more arcuate pieces and the padding member until a rounded cranium structure is achieved.

In one aspect, the padding member has two spaced temple engaging portions and an arcuate occipital portion extending continuously from one temple engaging portion to another and of increased width relative to the two temple engaging portions.

In one aspect, the anterior section is U-shaped and is configured with two spaced anteroposterior portions and a forehead engageable member which is provided with the widthwise adjustment mechanism, and the posterior section is U-shaped and is configured with two spaced anteroposterior portions, and wherein each of the anteroposterior portions of the anterior section is adjustably and releasably coupled with a corresponding anteroposterior portion of the posterior section with one of the lengthwise adjustment mechanisms.

In one aspect, the anterior section comprises two L-shaped elements each of which provided with one of the anteroposterior portions and a planar laterally extending element, and wherein the widthwise adjustment mechanism is configured to simultaneously displace the two laterally extending elements.

In one aspect, each of the two laterally extending elements is formed with a corresponding groove, and the forehead engageable member is integrally formed with an insert from which a screw connected thereto extends through the corresponding groove formed in each of the laterally extending elements, thereby facilitating widthwise adjustment of the orthosis upon displacement of a first of the laterally extending elements relative to a second of the laterally extending elements and upon securing a nut threadedly engaged with the screw.

In one aspect, one of the temple engaging portions of the padding member is attached to a corresponding anteroposterior portion of the anterior section.

In one aspect, each of the anteroposterior portions of the anterior section is formed with a groove within which an insert extends, thereby facilitating lengthwise adjustment of the orthosis.

In one aspect, each of the at least one lengthwise adjustment mechanism comprises a resilient clamping unit.

In one aspect, the headpiece further comprises a curved brace inserted within, and attached to, a corresponding arcuate piece, said curved brace being pivotally connected by a transversal pivot to a protruding portion of an appendage fixedly attached to an insert to facilitate angular adjustment of the corresponding arcuate piece about a lateral axis.

In one aspect, the headpiece further comprises a sensor module fitted between at least one of the arcuate pieces and the padding member or at different locations along an internal or external surface of the headpiece and in force transmitting relation therewith, to continuously measure data related to mechanical pressure to which the skull of the infant is exposed.

In one aspect, the sensor module comprises an array of distributed sensors for detecting a force exerted at a corresponding skull region, a microcontroller for receiving and processing data signals derived from each of said sensors for measuring said force, and a battery for powering said microcontroller and each of said sensors.

In one aspect, the sensor module has an arcuate configuration.

A diagnostic and therapeutic apparatus for detecting and treating torticollis or cervical muscle imbalance or any other impairment related to head control and head movements, comprises a headpiece capable of encircling, and being secured to, regions of a subject's head, a microcontroller, and a single orientation sensor exclusively which is mounted on said headpiece and is in data communication with said microcontroller to continuously or periodically measure data related to an instantaneous orientation of the subject's head, as well as changes in said orientation over time, wherein said orientation sensor is an inertial measurement unit (IMU) that comprises at least one accelerometer, wherein said microcontroller is configured to generate a gravity vector from said IMU, to determine the instantaneous orientation of the subject's head relative to the generated gravity vector, and to thereby determine a location of asymmetrical cervical muscles.

In one aspect, the apparatus further comprises an array of distributed pressure sensors in data communication with the microcontroller which are mounted on the headpiece, for detecting a force exerted at a corresponding head region, wherein the microcontroller is configured to determine that the subject is in a lying position when at least one of the pressure sensors outputs data signals and to angularly shift the generated gravity vector by 90 degrees.

In one aspect, the apparatus further comprises a resistance applying element coupled to a selected region of a posterior section of the headpiece which is contralaterally located with respect to the determined location of asymmetrical cervical muscles, said resistance applying element configured to induce tensioning of the asymmetrical cervical muscles until the subject's head achieves a balanced condition.

In one aspect, each of the pressure sensors is arched.

The apparatus may be adapted to obtain early diagnosis and treating of torticollis or any other impairment related to head control and head movements, and may further comprise an electronic module with an orientation sensor (such as a gyroscope and/or a 3-D accelerometer), memory and operating software that continuously measures and records the instantaneous orientation of the infant's head (for example, while lying on his back), as well as changes in the orientation over time.

Optionally, the measured data may be stored and processed in a computational cloud, for allowing display to end users and access by other applications.

A method for diagnosing a skull deformity or a cervical muscle imbalance comprises the steps of providing a headpiece to which is mounted a forehead engaging member, a microcontroller, an orientation sensor and a plurality of identical pressure sensors for being positioned at spatially different head locations; securing said headpiece to the head of a subject while ensuring that one of the pressure sensors is aligned with the forehead engaging member; by said microcontroller, identifying and receiving data from said orientation sensor and said plurality of pressure sensors; performing a calibration operation by generating a vertical reference line that extends from the aligning sensor upon determining that the aligning sensor senses a highest contact pressure among all of the plurality of pressure sensors; acquiring data representative of a current head position relative to the reference line from the orientation sensor; verifying the acquired head position by determining whether the aligning sensor senses the highest contact pressure; readjusting said headpiece until the aligning sensor senses the highest contact pressure; storing the verified head position data; and outputting data representative of most frequent head positions.

BRIEF DESCRIPTION OF THE DRAWINGS

In the Drawings:

FIG. 4A is a side view of the cranial orthosis of FIG. 1, schematically illustrating angular and lengthwise adjusting modes;

FIG. 4B is an anterior view of the cranial orthosis of FIG. 1, schematically illustrating a widthwise adjusting mode;

FIG. 4C is a plan view of the cranial orthosis of FIG. 1, schematically illustrating lengthwise and widthwise adjusting modes;

5

Figure 7:
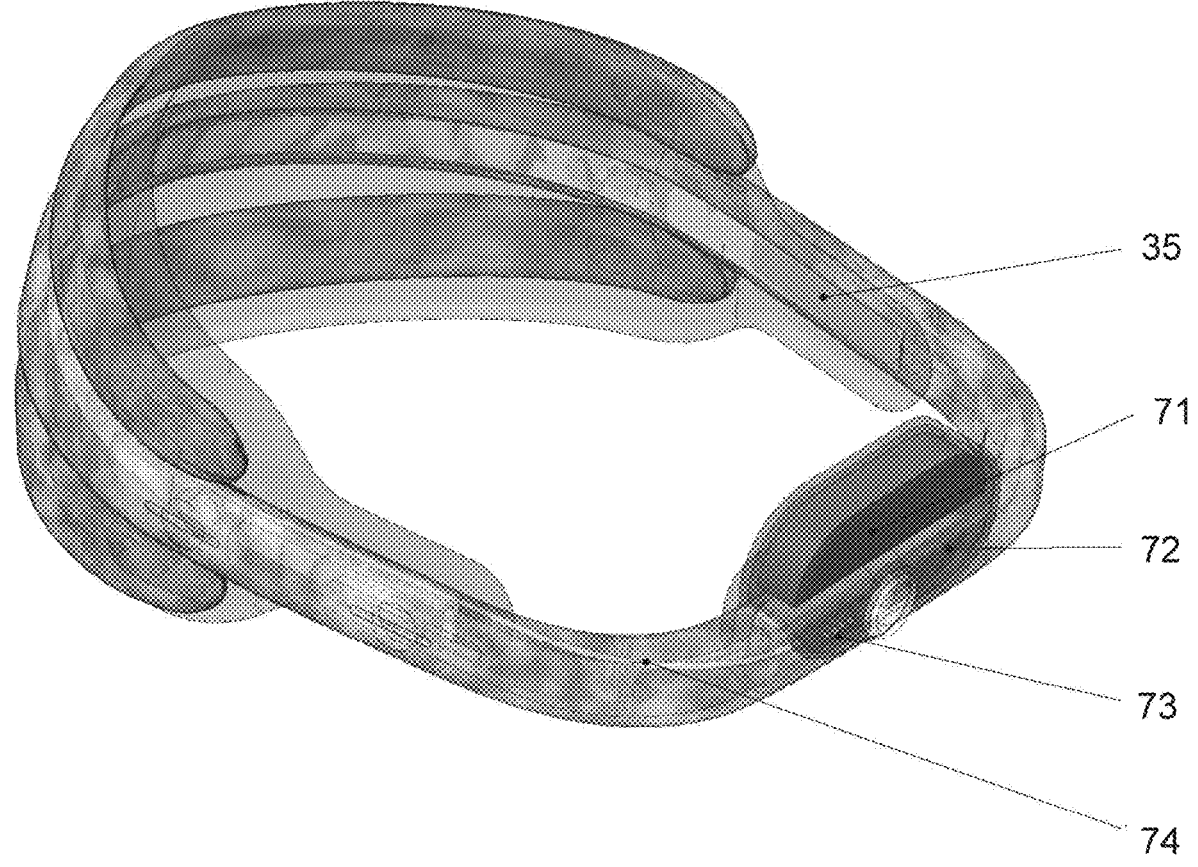
Figures 8, 9:
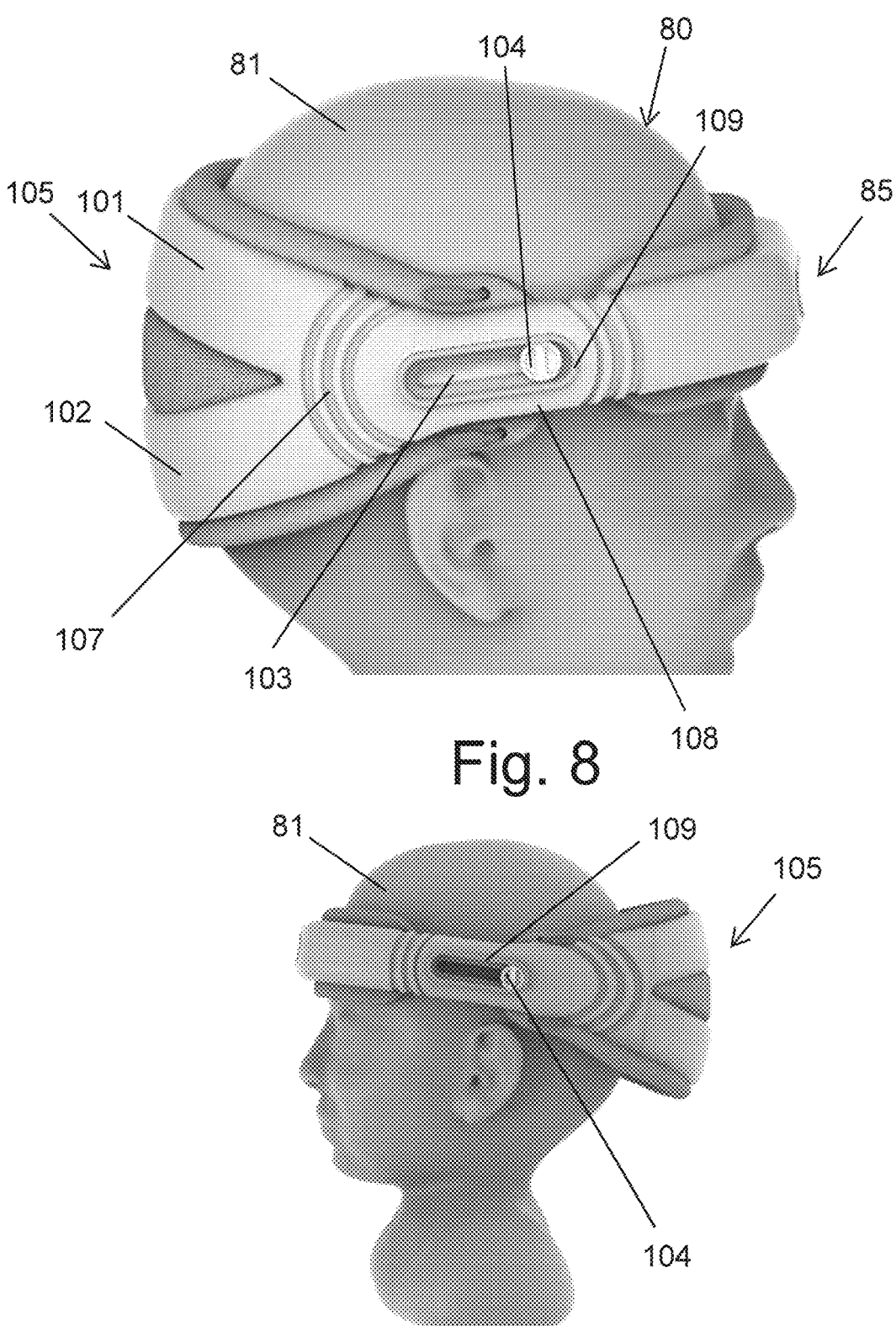
Figure 10A:
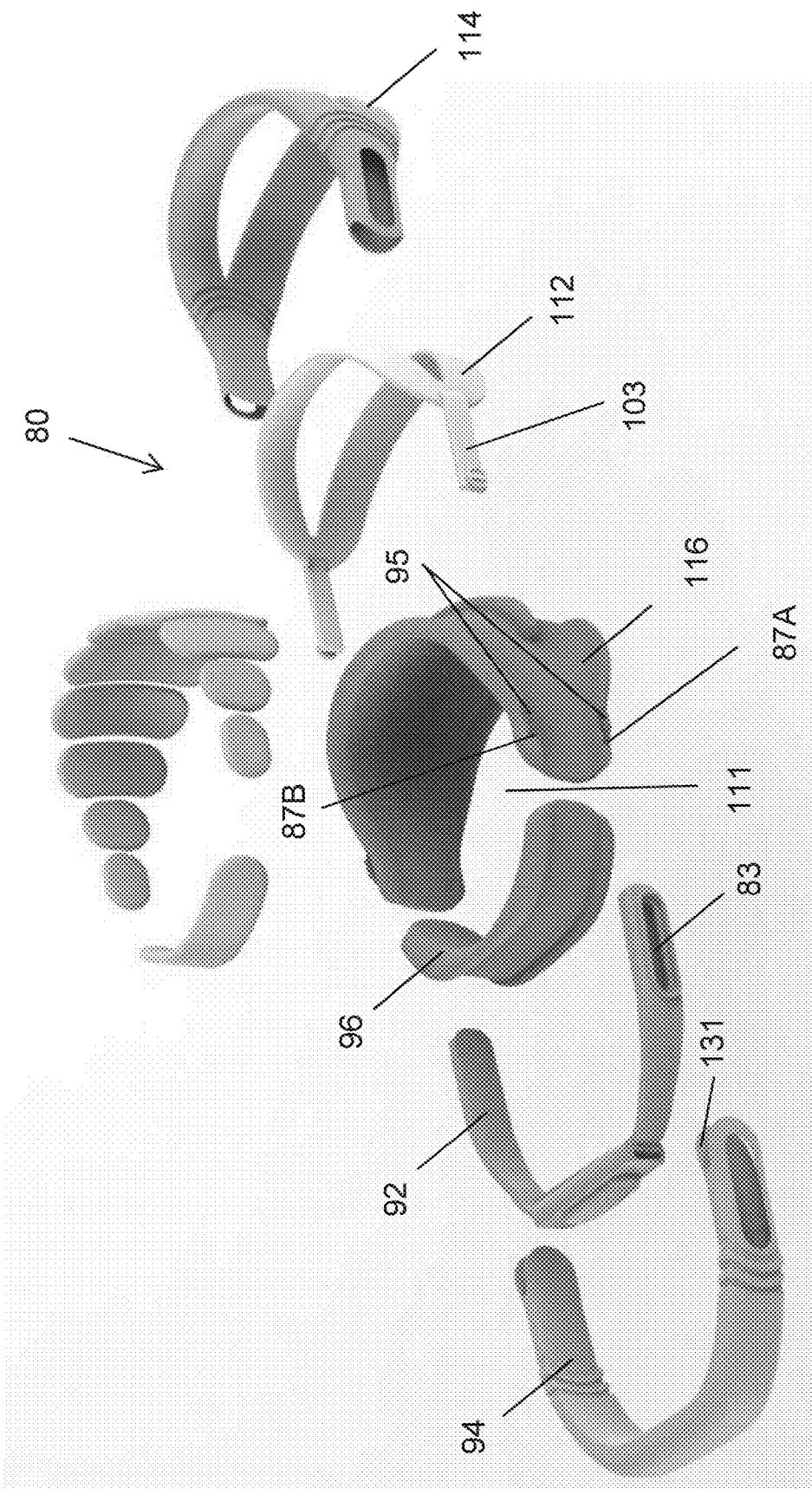
Figure 10B:
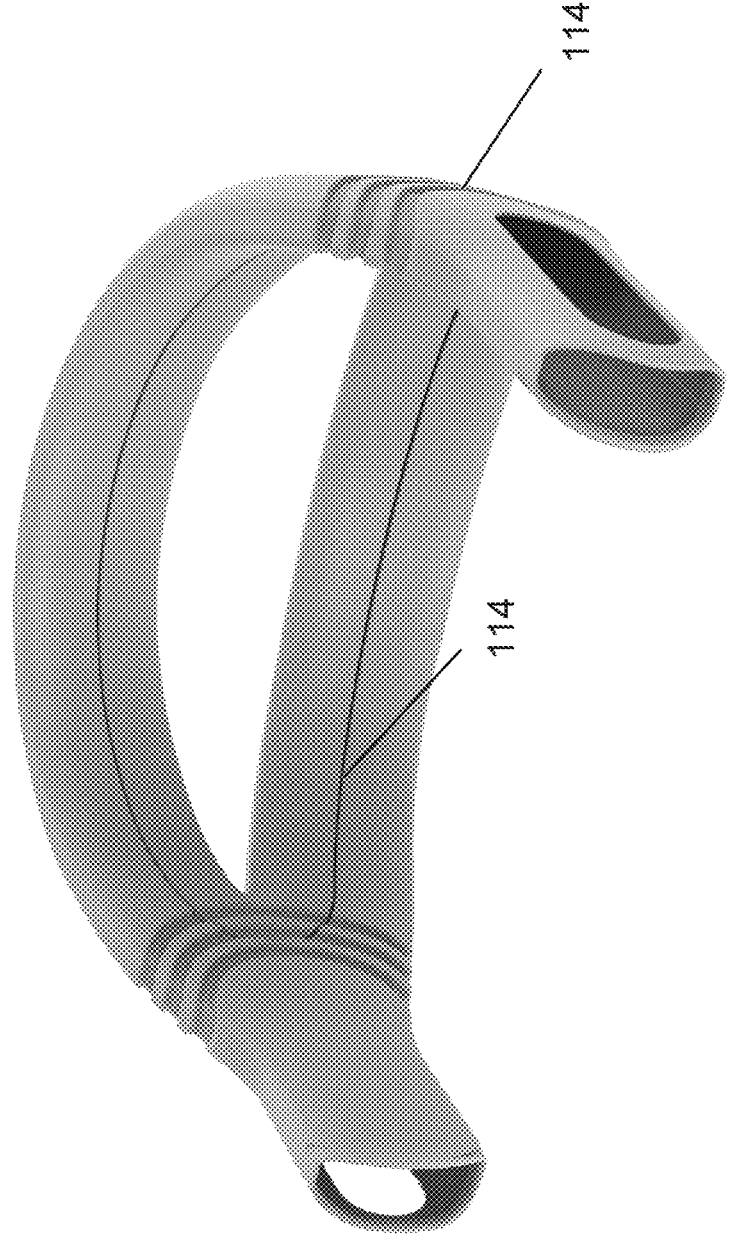
Figure 11:
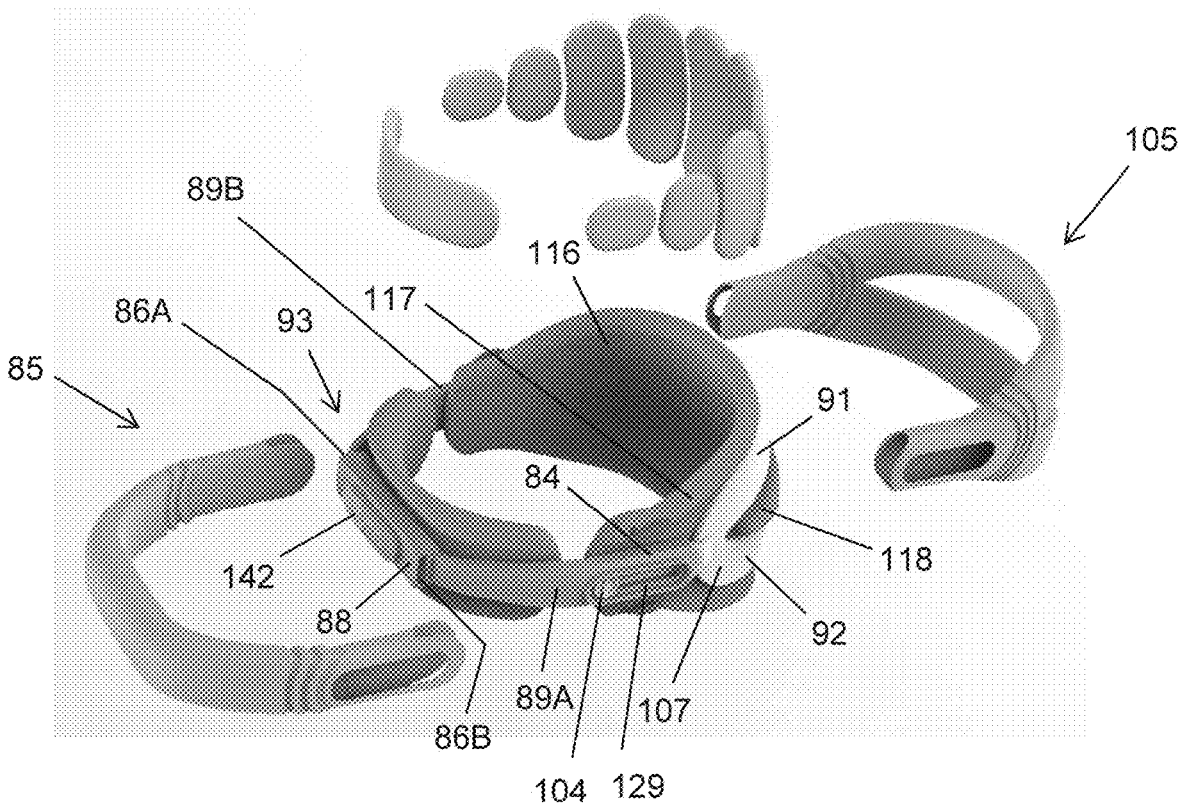
Figure 12:
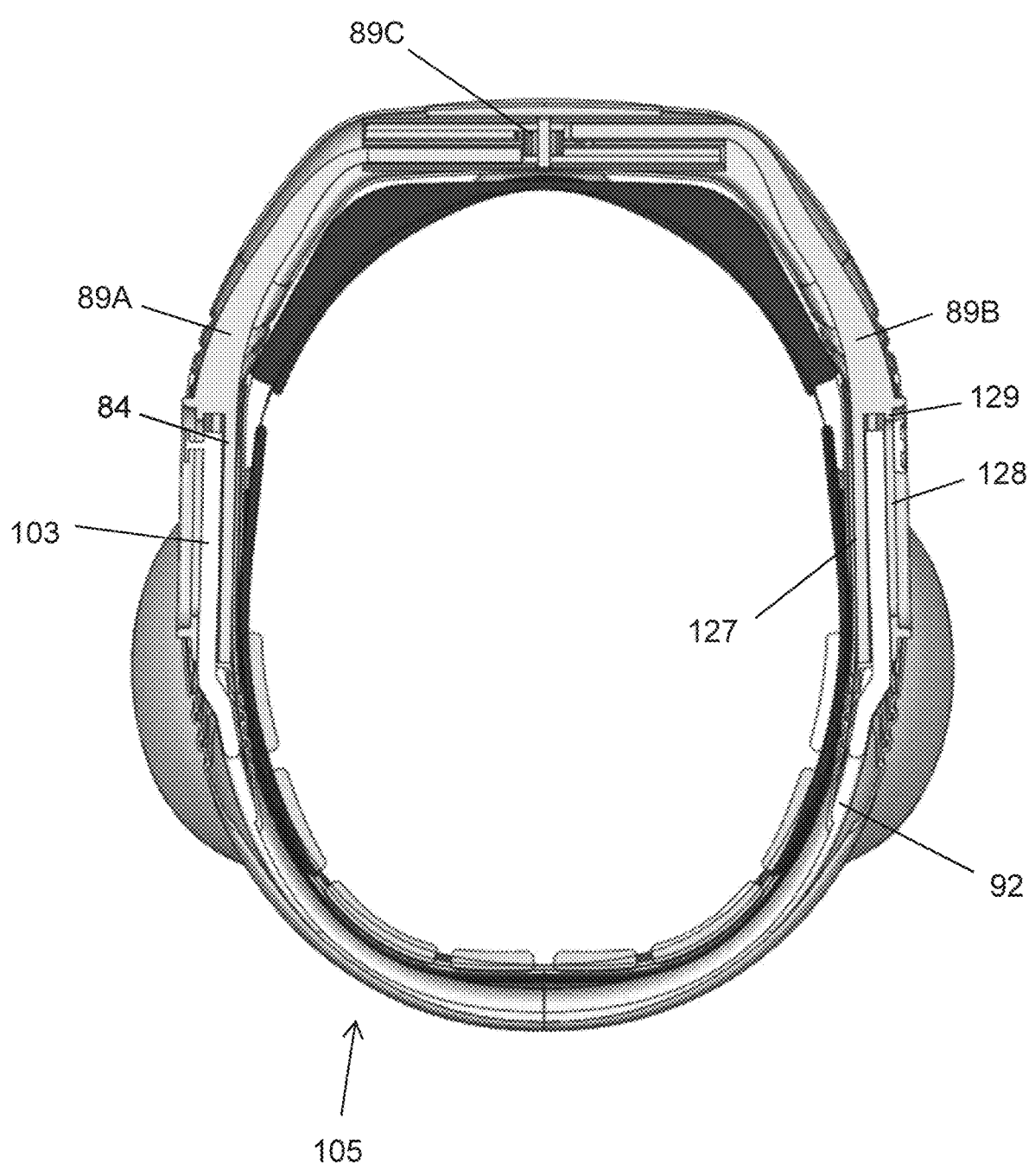
Figure 13A:
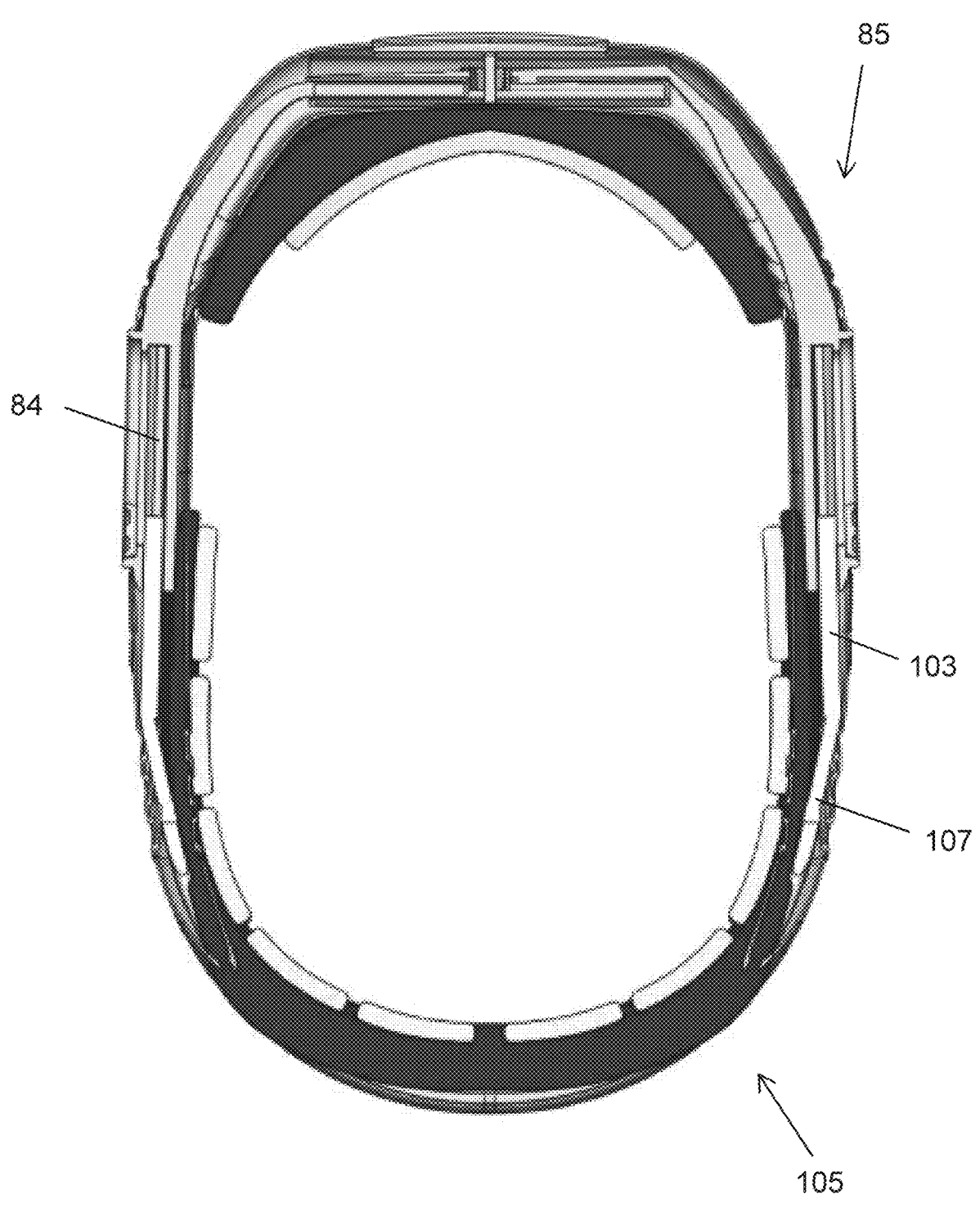
Figure 13B:
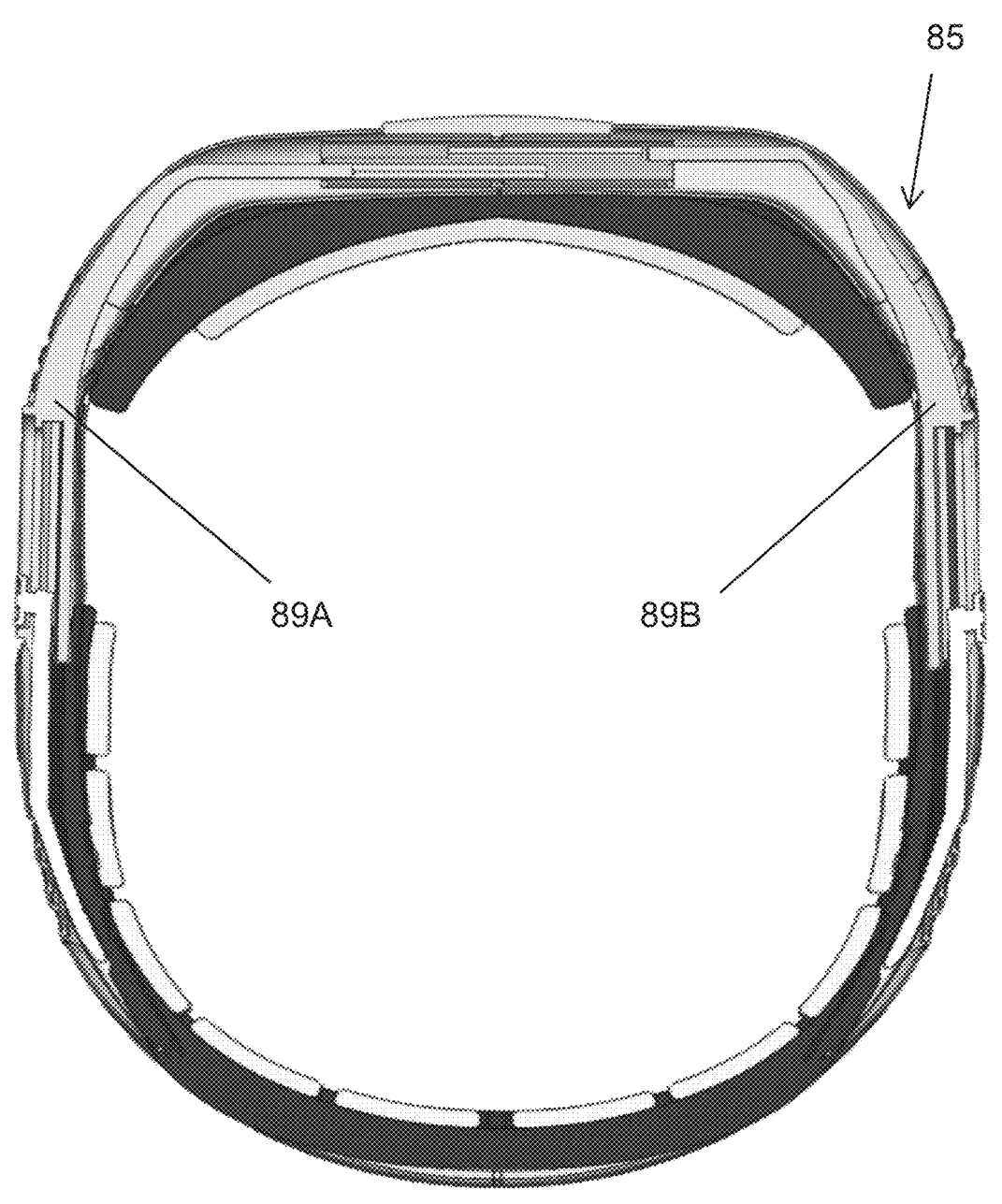
Figure 14:
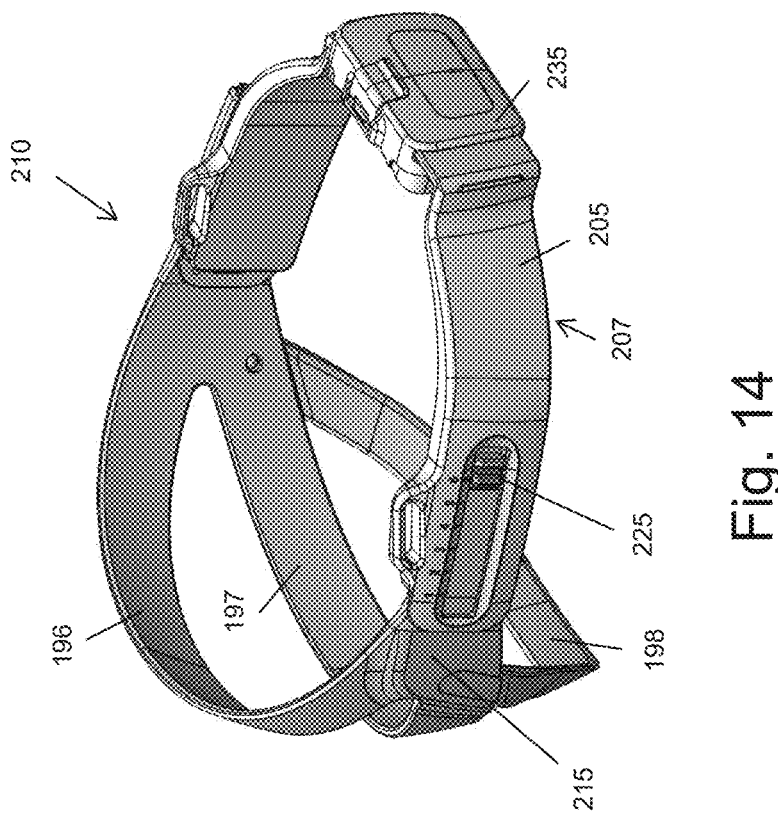
Figure 15:
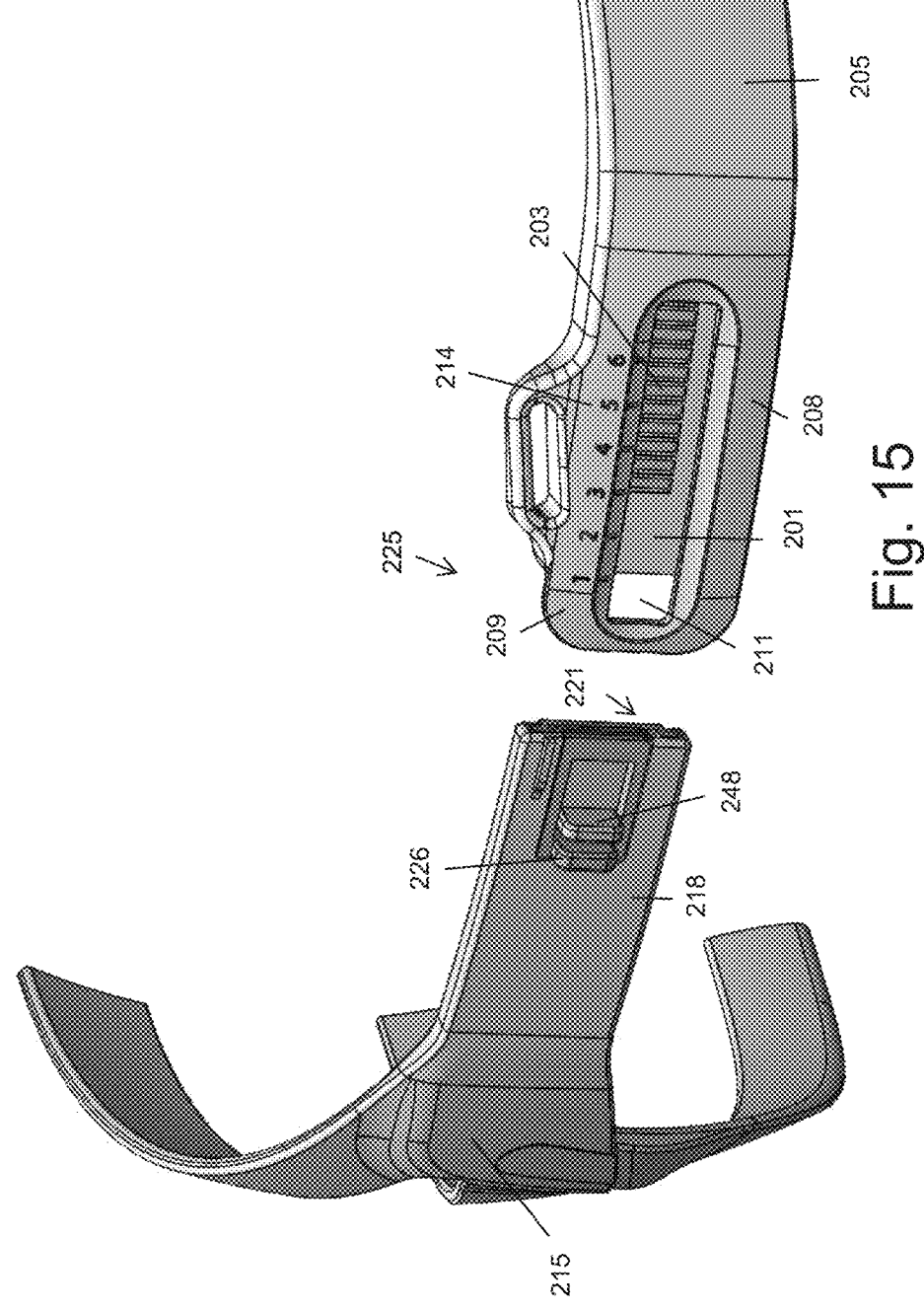
Figure 16:
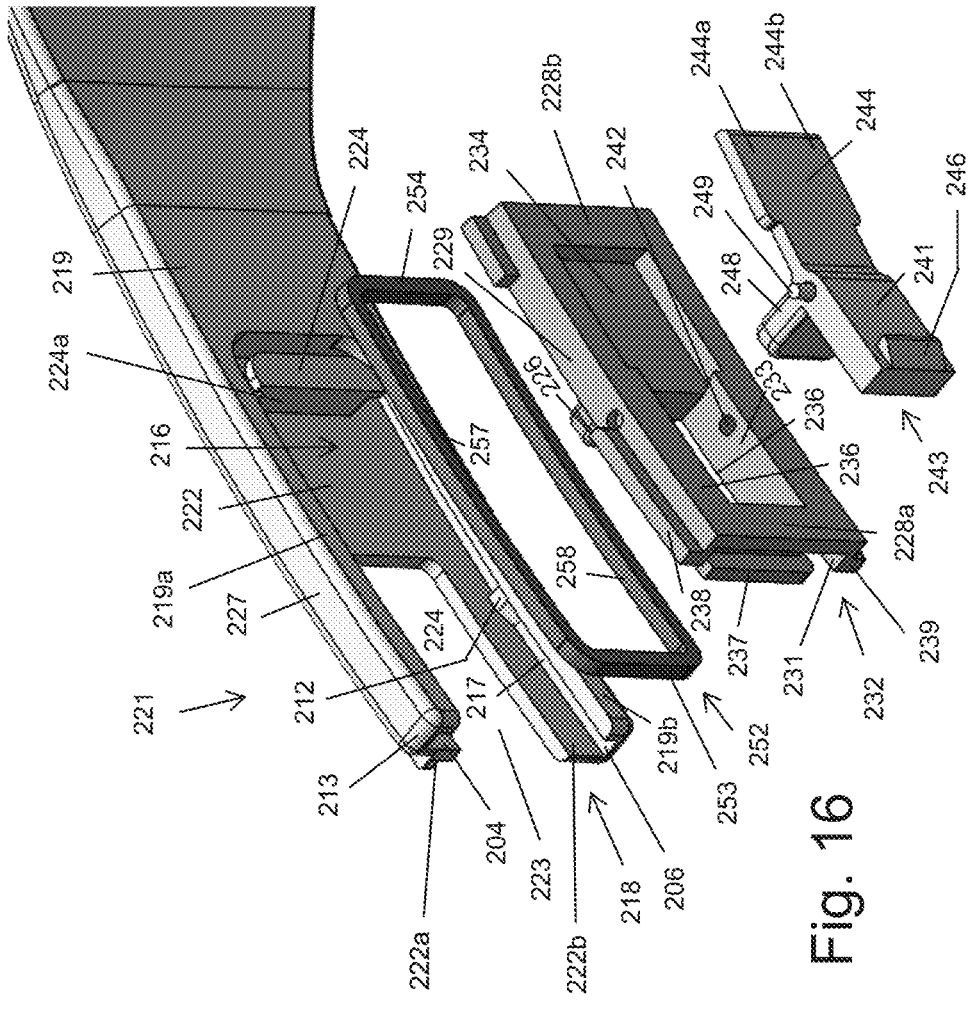
Figures 17A, 17B:
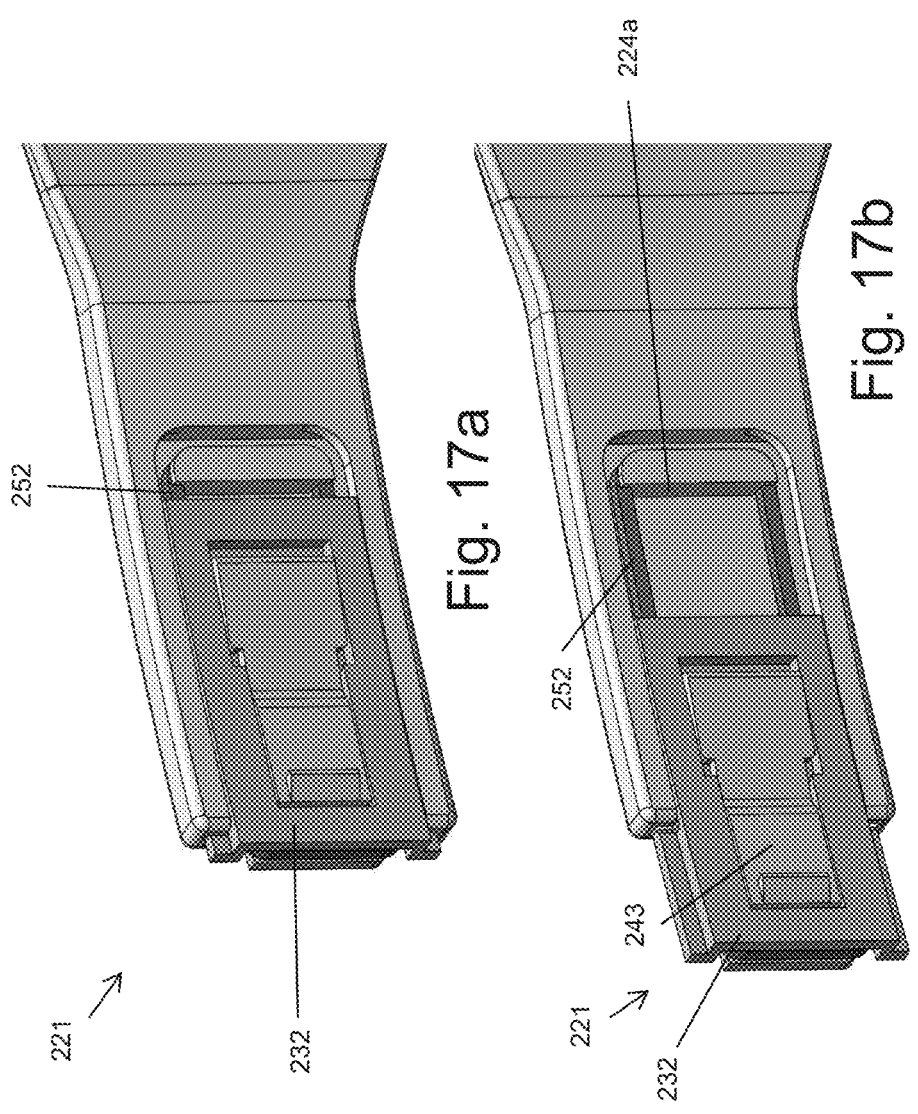
Figures 18A, 18B:
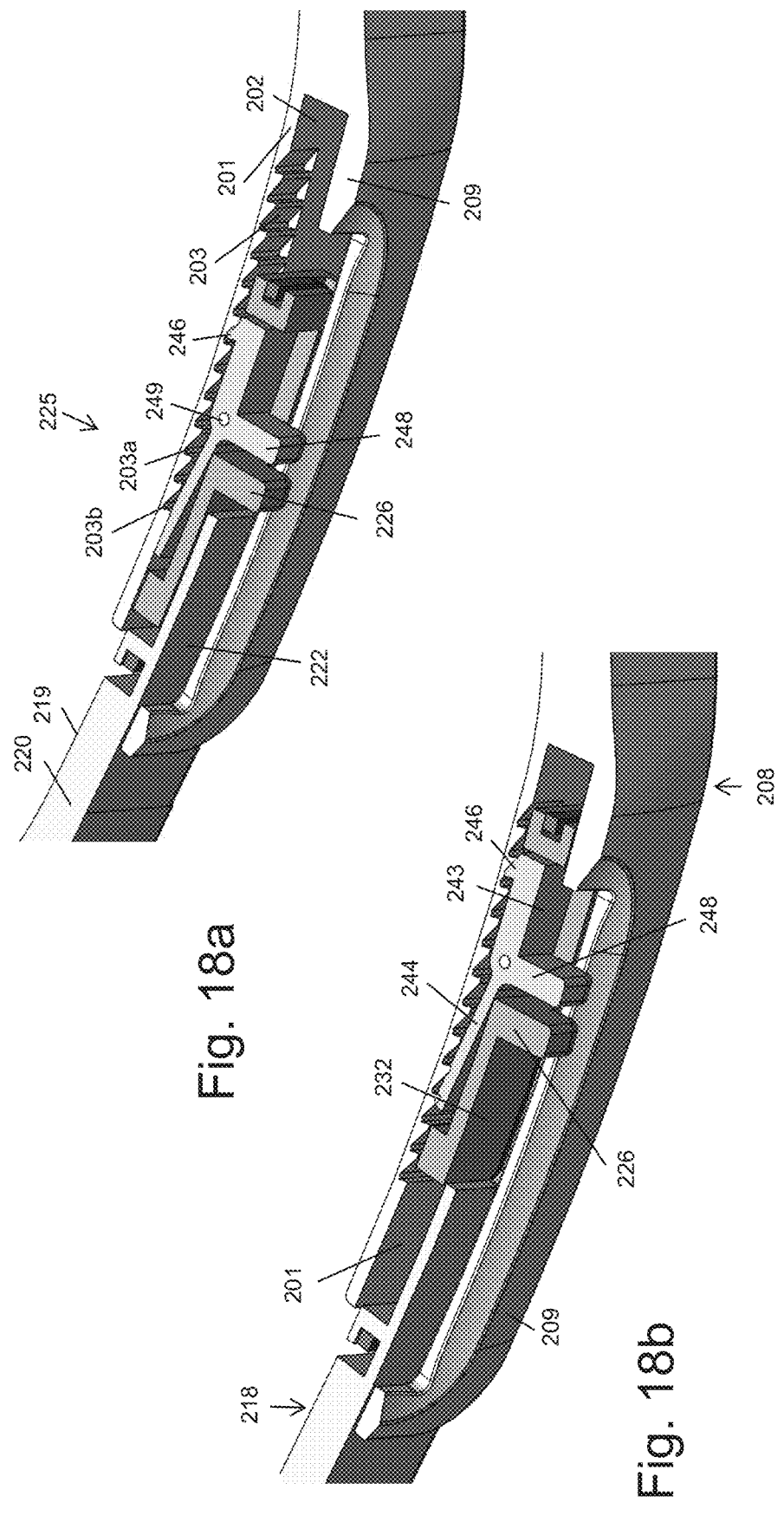
Figure 19:
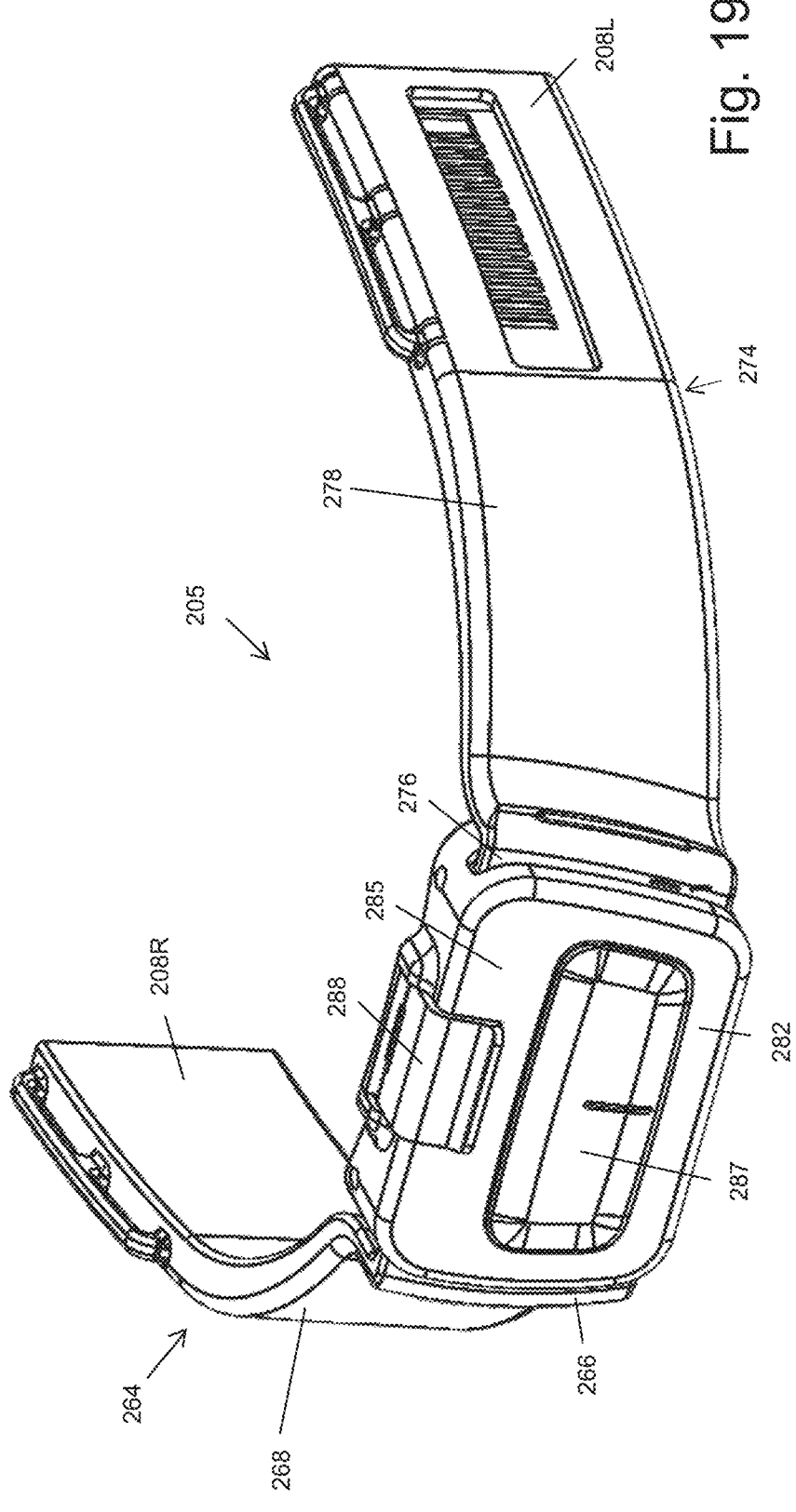
Figure 20:
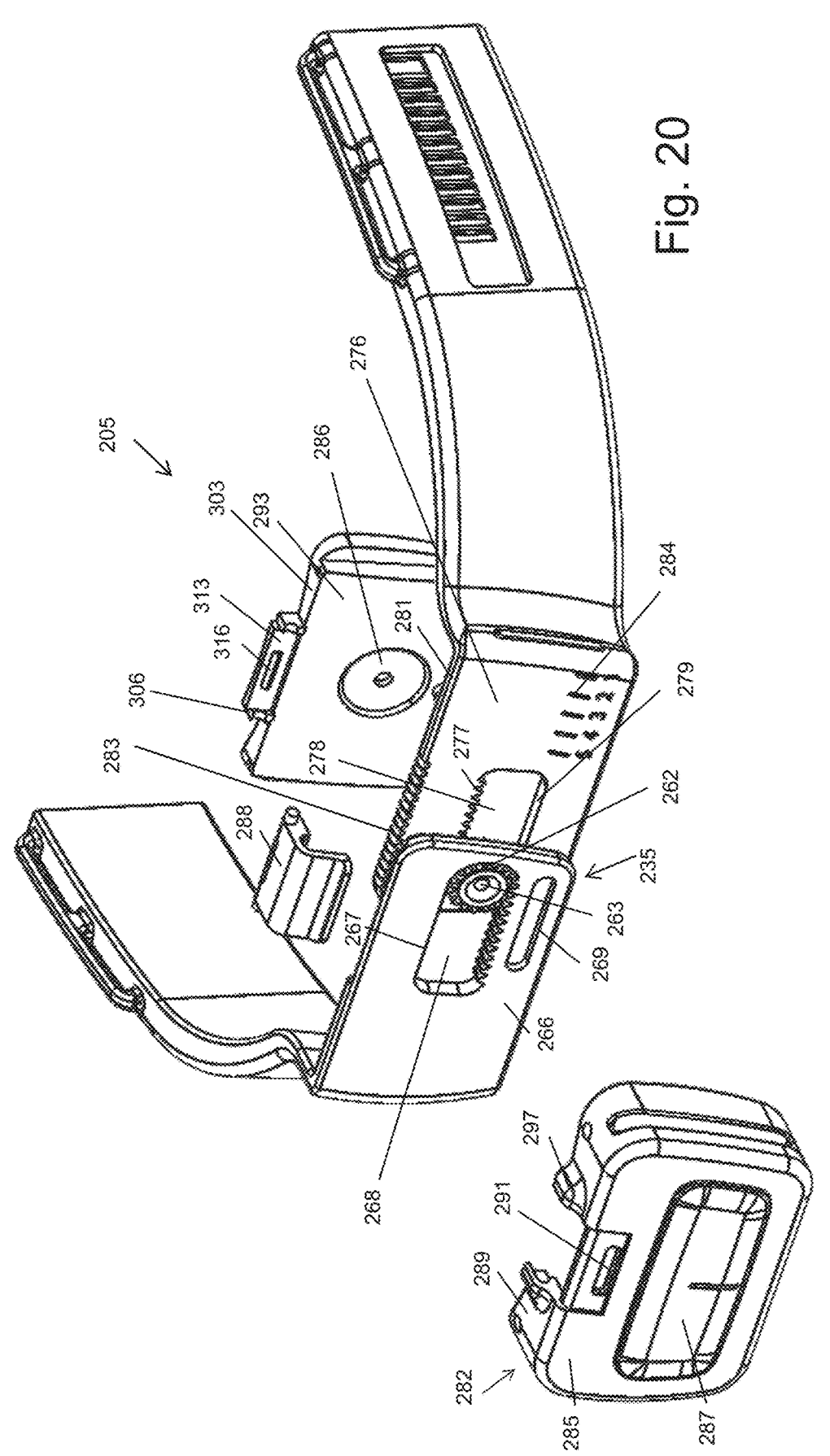
Figure 21A:
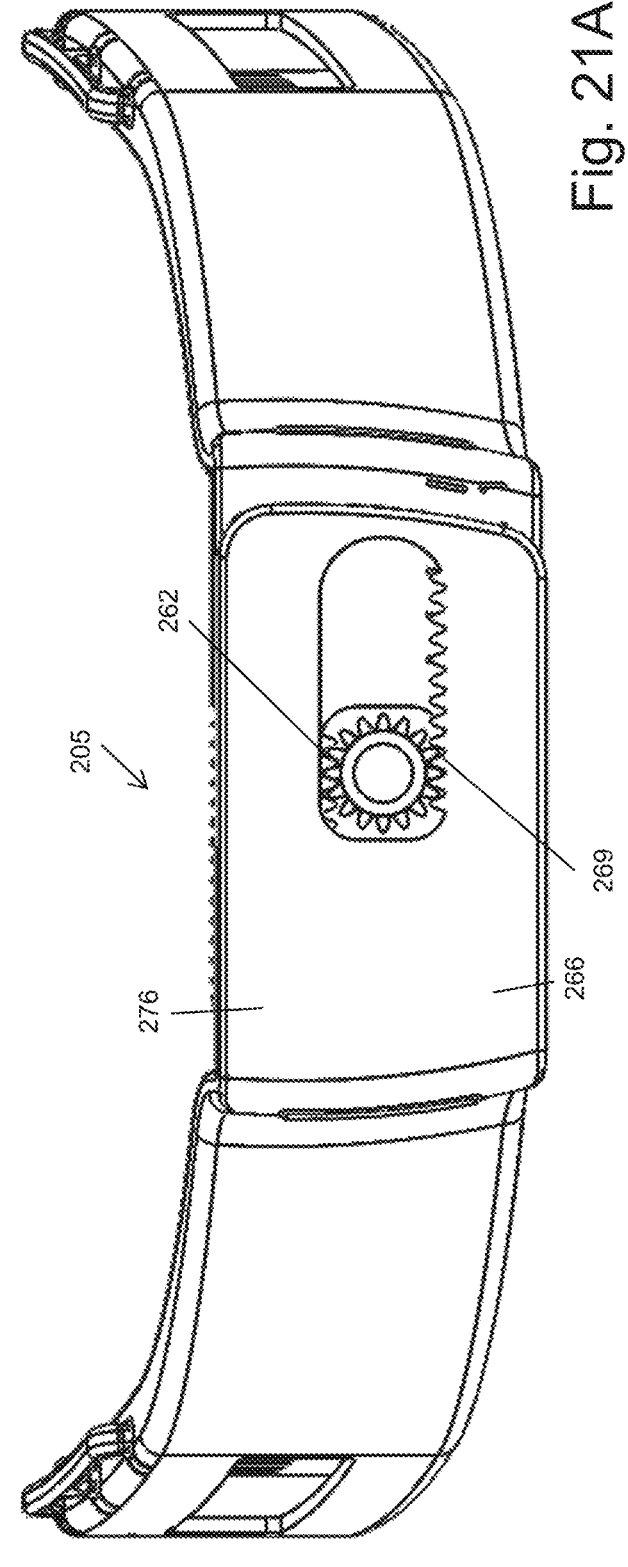
Figure 21B:
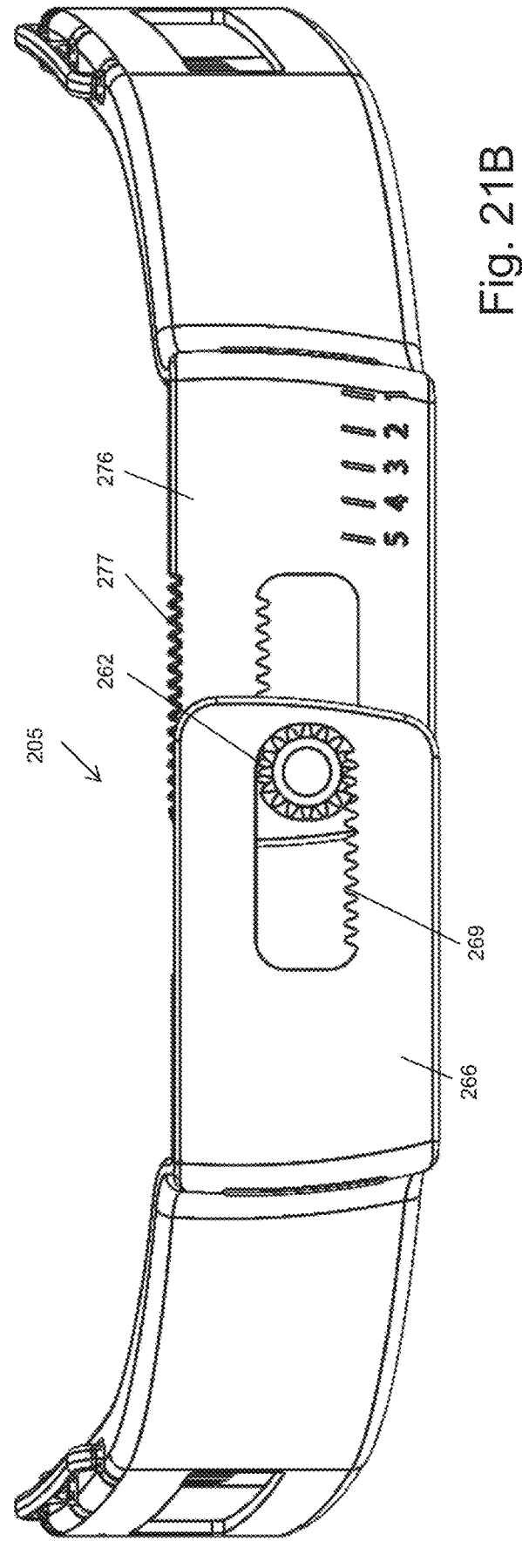
Figure 22A:
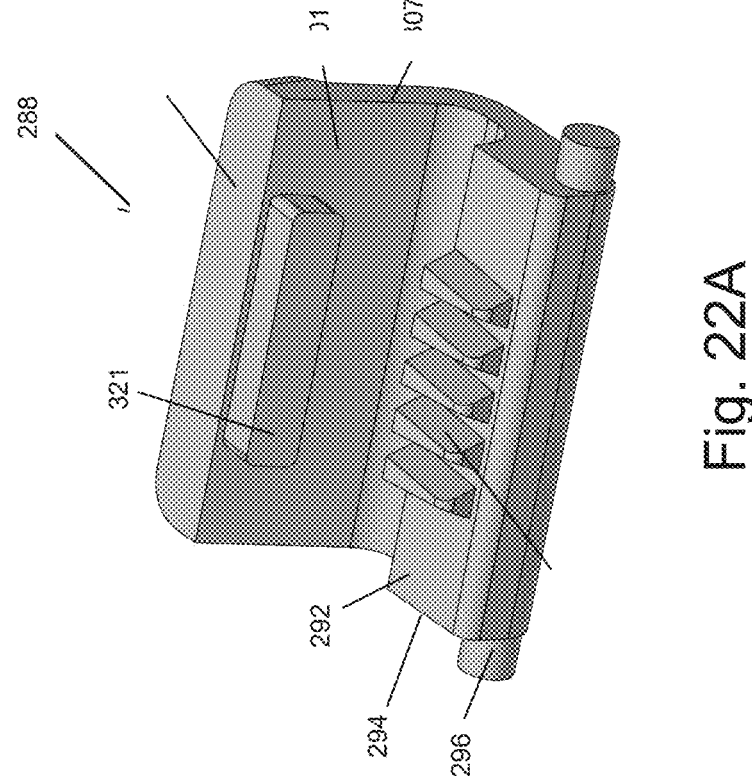
Figure 22B:
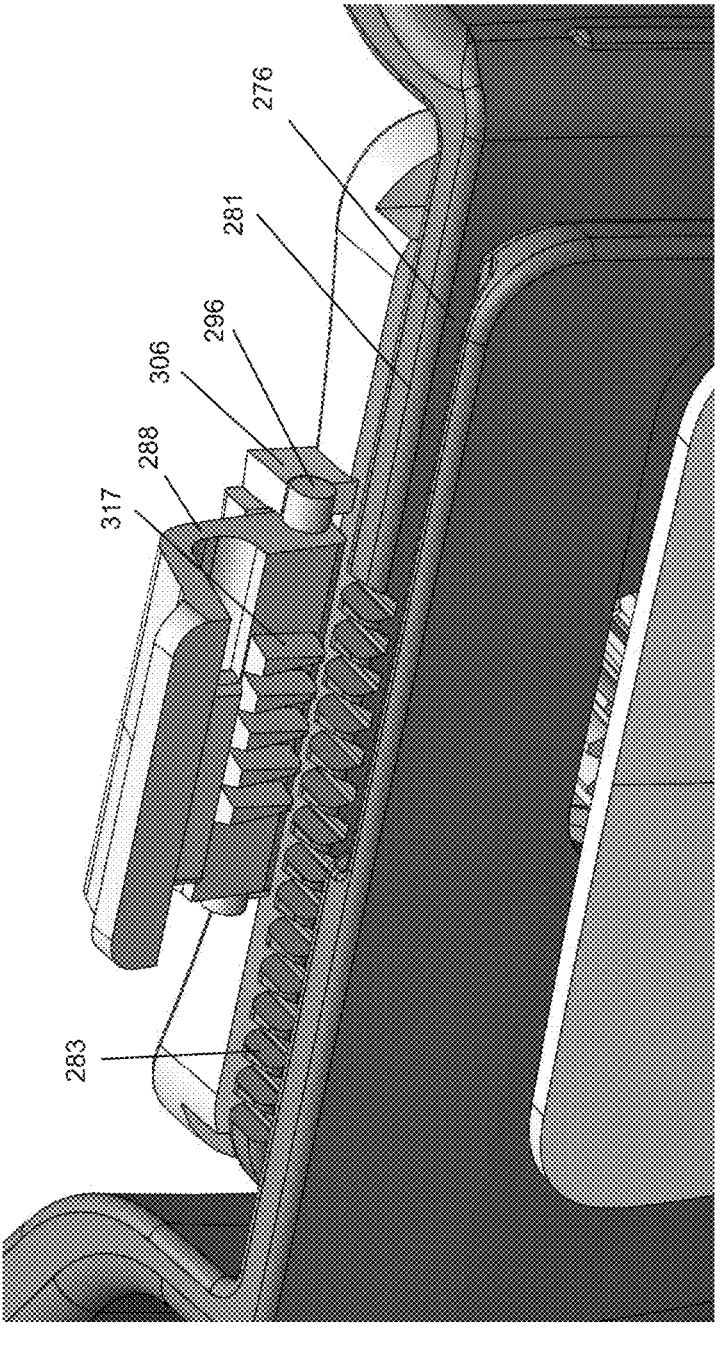
Figure 22C:
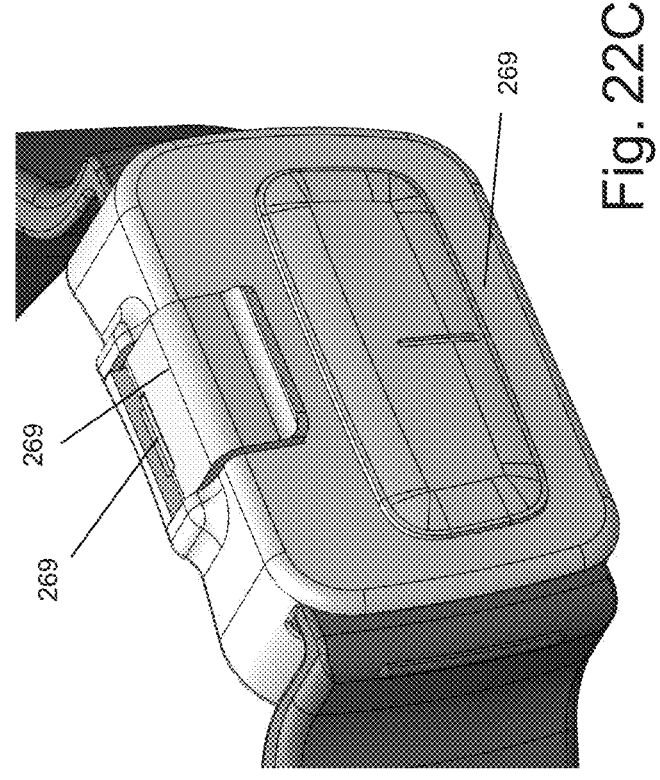
Figure 23B:
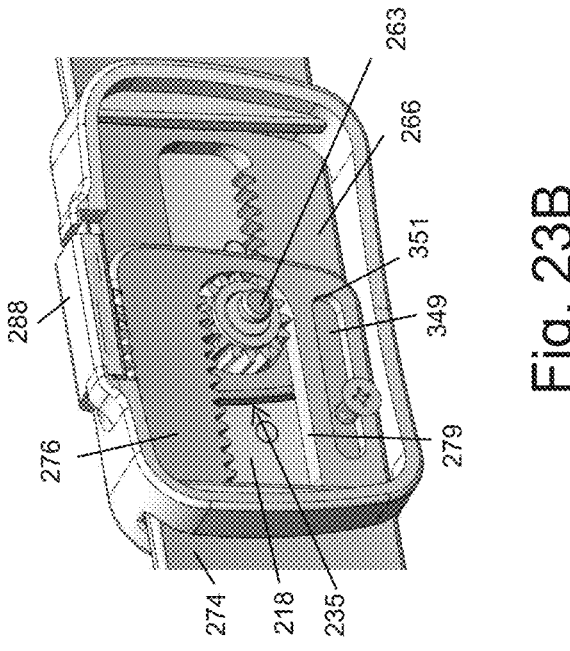
Figure 23A:
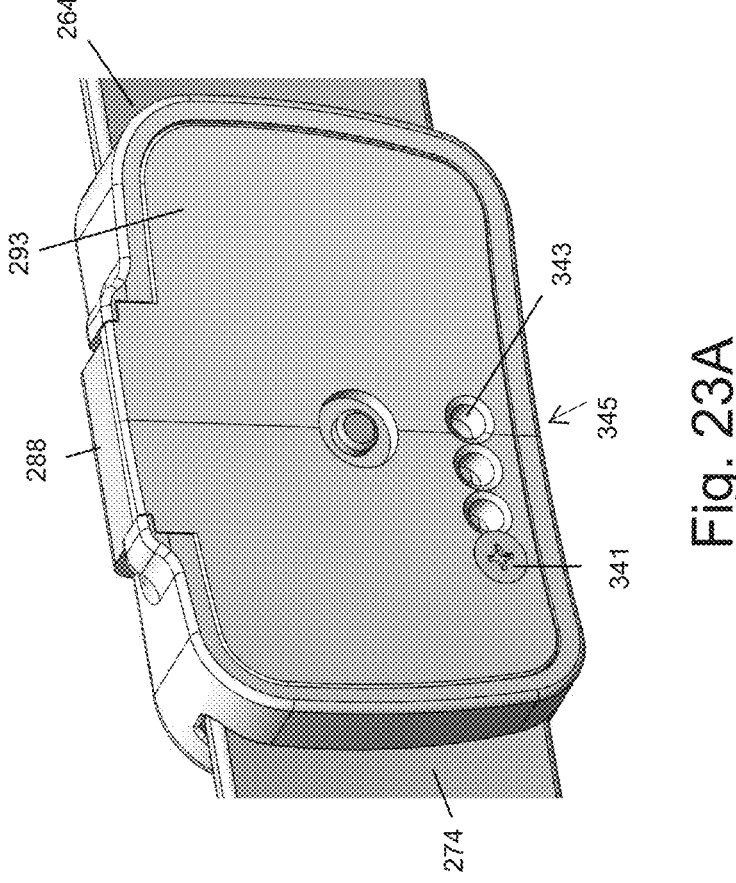
Figure 24:
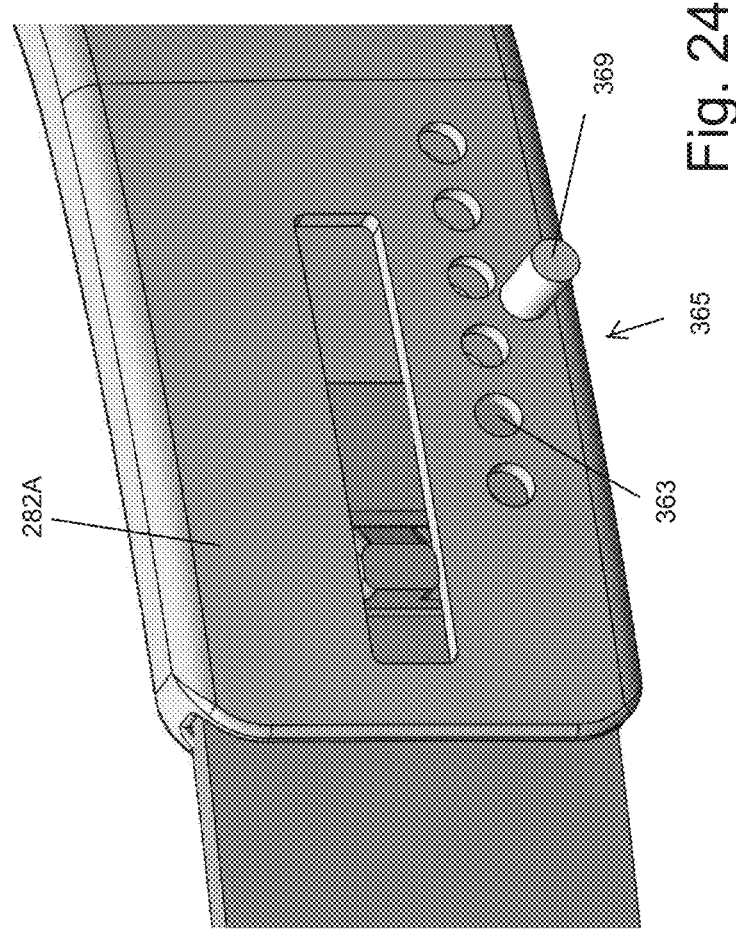

FIG. 7 illustrates another embodiment, according to which the anterior section (shown in FIG. 1) of the adjustable cranial orthosis comprises an orientation sensor;

FIG. 8 is a perspective view of another embodiment of a cranial orthosis secured to an infant's skull, when adjusted to a minimum length;

FIG. 9 is a perspective view of the orthosis of FIG. 8 secured to an infant's skull, when adjusted to a maximum length;

FIG. 10A is a perspective view of an exploded view of the orthosis of FIG. 8;

FIG. 10B illustrates an incision in the posterior protective sheath that allows inserting the posterior support frame;

FIG. 11 is a perspective view of the orthosis of FIG. 8 when assembled without the protective sheaths and when unsecured to an infant's skull;

FIG. 12 is a horizontal cross sectional view of the orthosis of FIG. 8, when adjusted to a minimum length;

FIG. 13A is a horizontal cross sectional view of the orthosis of FIG. 8, when adjusted to a maximum length;

FIG. 13B illustrates posterior section of FIG. 13A, following further displacement of the two L-shaped elements laterally, to gain extra width;

FIG. 14 is a perspective view of a cranial orthosis according to another embodiment;

FIG. 15 is a perspective view of a portion of a posterior section and of an anterior section of the orthosis of FIG. 14 when decoupled from each other;

FIG. 16 is an exploded view of a resilient clamping unit usable in conjunction with the orthosis of FIG. 14;

FIGS. 17A and 17B are a perspective view from the inner side of the resilient clamping unit of FIG. 16, showing the pawl holder in retracted in extended positions, respectively, when the pawl is disengaged from rack teeth;

FIGS. 18A and 18B are a perspective view of a lengthwise adjustment mechanism in transverse cross sectional view that includes the resilient clamping unit pawl of FIG. 16 when the pawl is engaged with one of the rack teeth, showing the pawl in less advanced and more advanced positions, respectively;

FIG. 19 is a perspective view of an assembled anterior section usable in conjunction with the orthosis of FIG. 14;

FIG. 20 is an exploded view of portions of the anterior section of FIG. 19;

FIGS. 21A and 21B are a perspective view of the anterior section of FIG. 19 when set to two different widths, respectively, shown without the housing members;

FIG. 22A is a perspective view of a pivotal locking handle usable in conjunction with the anterior section of FIG. 19, shown when detached therefrom;

FIG. 22B is a perspective view of the locking handle of FIG. 22A, shown when pivotally attached in an unlocked position to a posterior housing member and without an anterior housing member;

FIG. 22C is a perspective view of the locking handle of FIG. 22A, shown when pivoted to a locked position while being supported by an anterior housing member;

FIG. 23A is a perspective view of a posterior housing member usable in conjunction with the anterior section of FIG. 19 when coupled with an anterior housing member, showing elements of a lateral displacement limiting unit;

FIG. 23B is a perspective view of the anterior housing member of FIG. 23A when the posterior housing member is decoupled therefrom, showing other elements of the lateral displacement limiting unit;

FIG. 24 is a perspective view of an anterior housing member usable in conjunction with the anterior section of

6

Figure 25B:
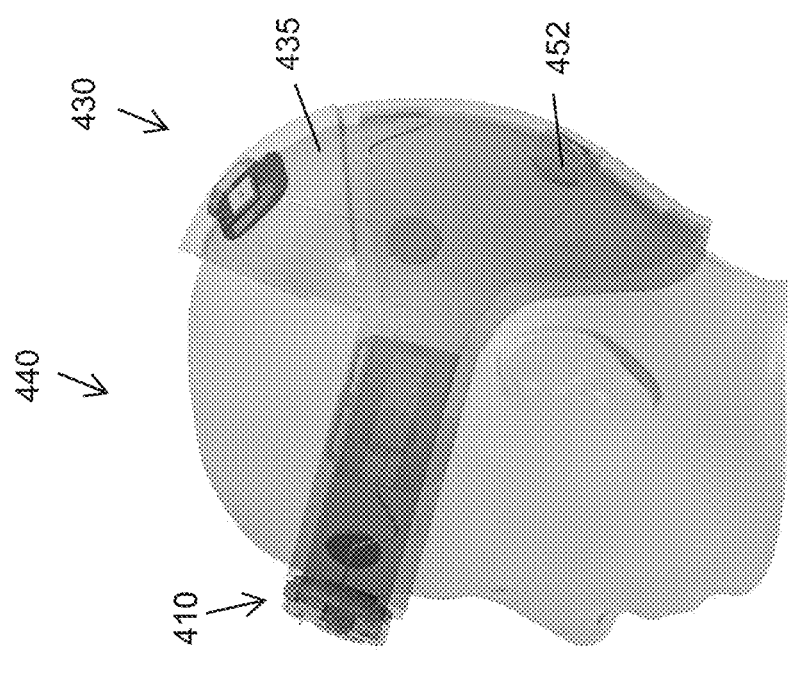
Figure 25A:
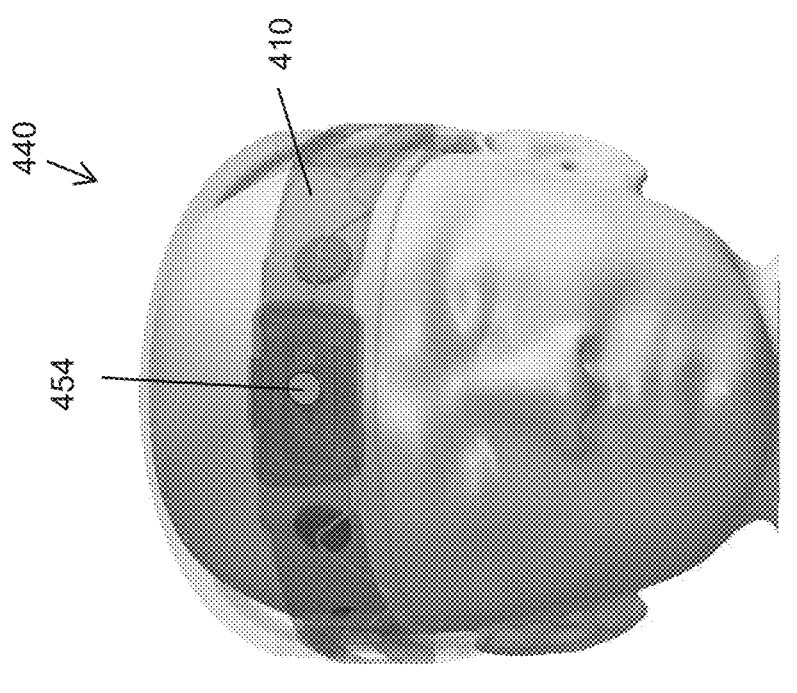
Figure 25D:
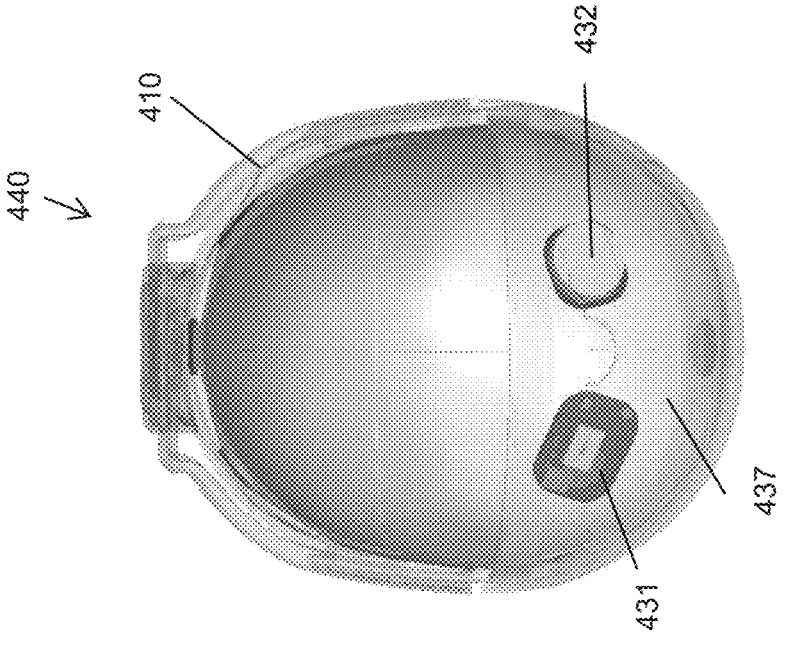
Figure 25C:
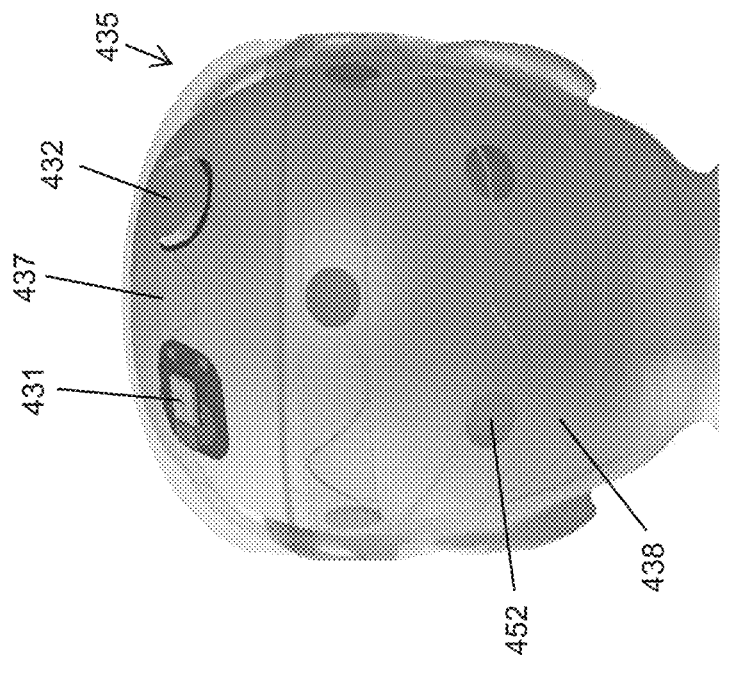
Figure 26B:
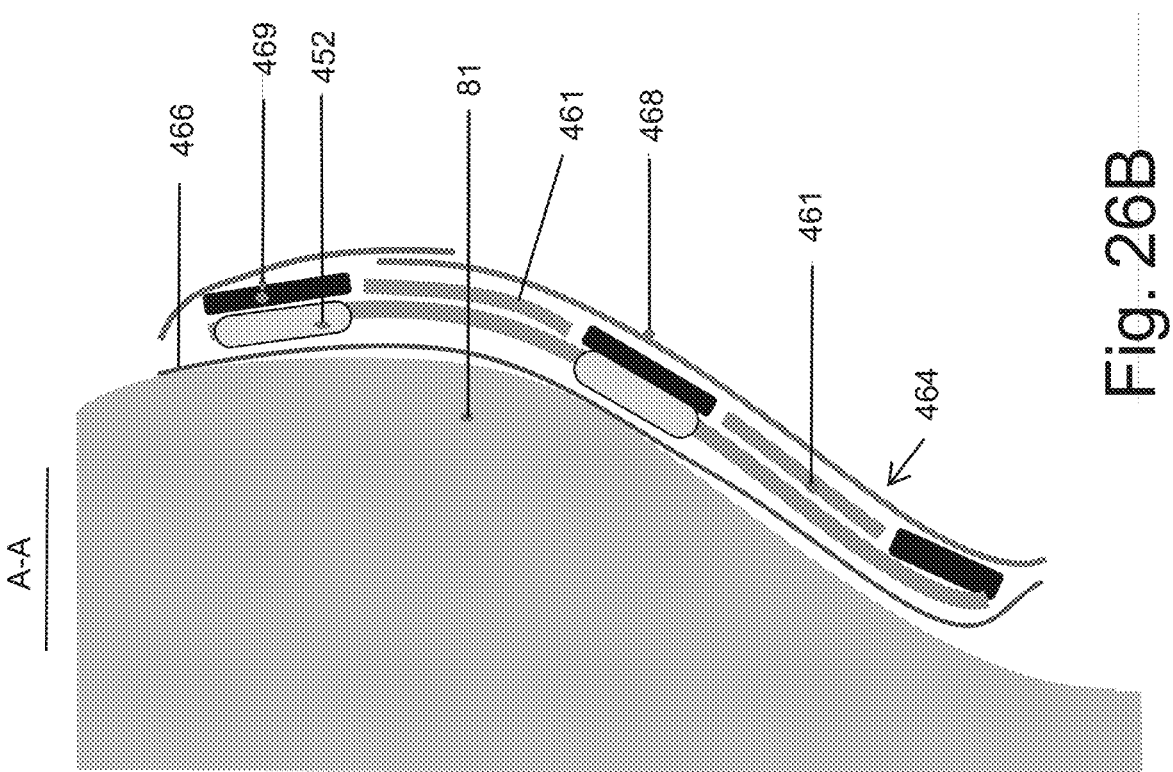
Figure 26A:
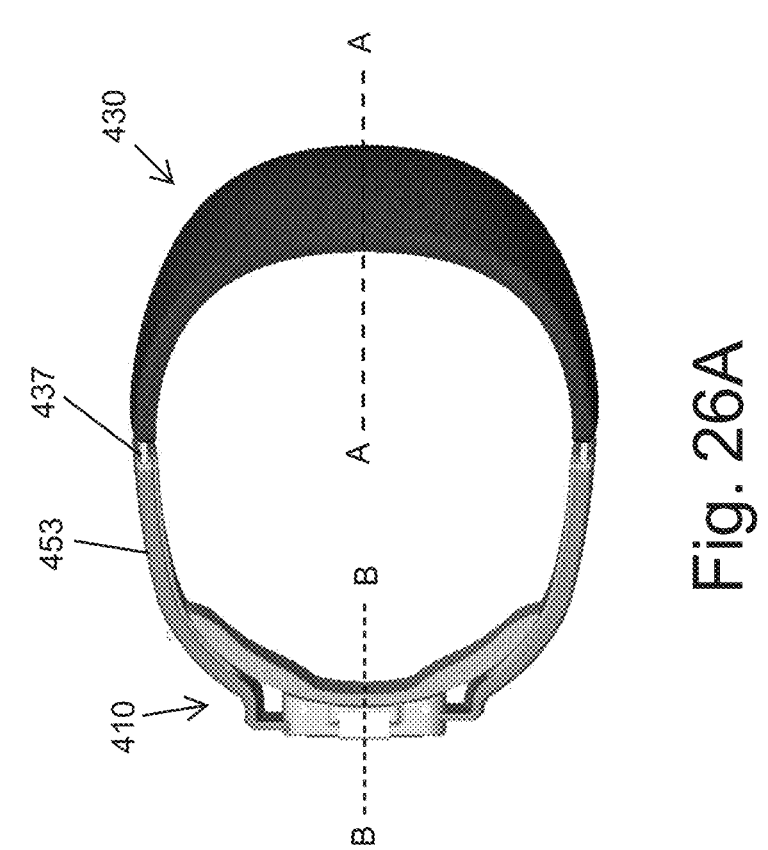
Figure 26C:
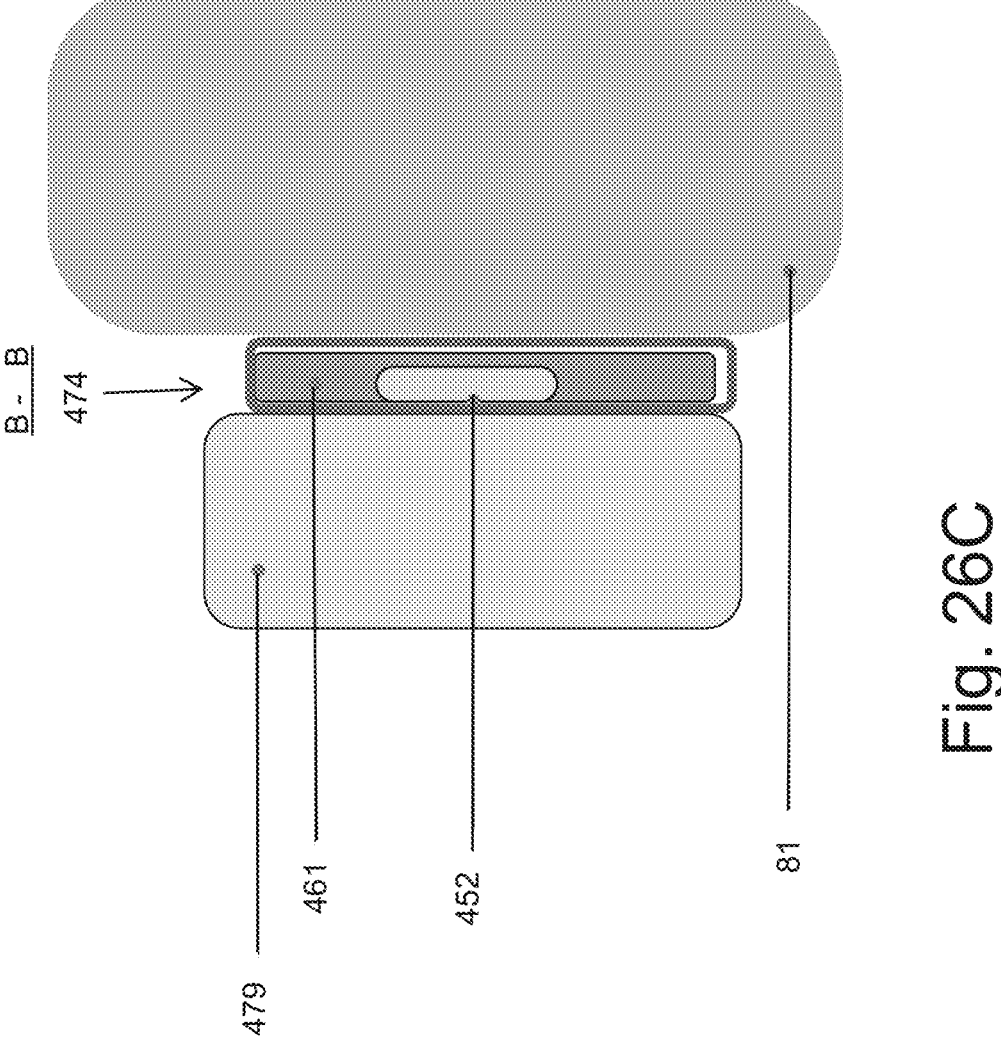
Figure 28A:
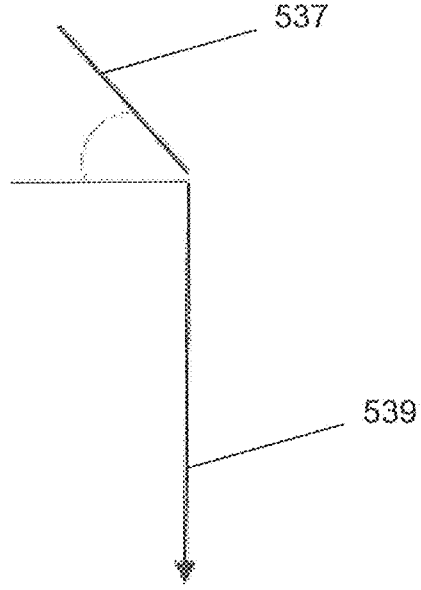
Figure 28B:
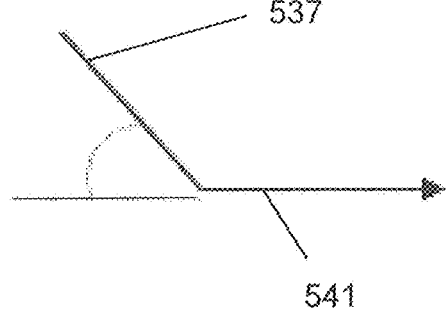
Figures 29A, 29B:
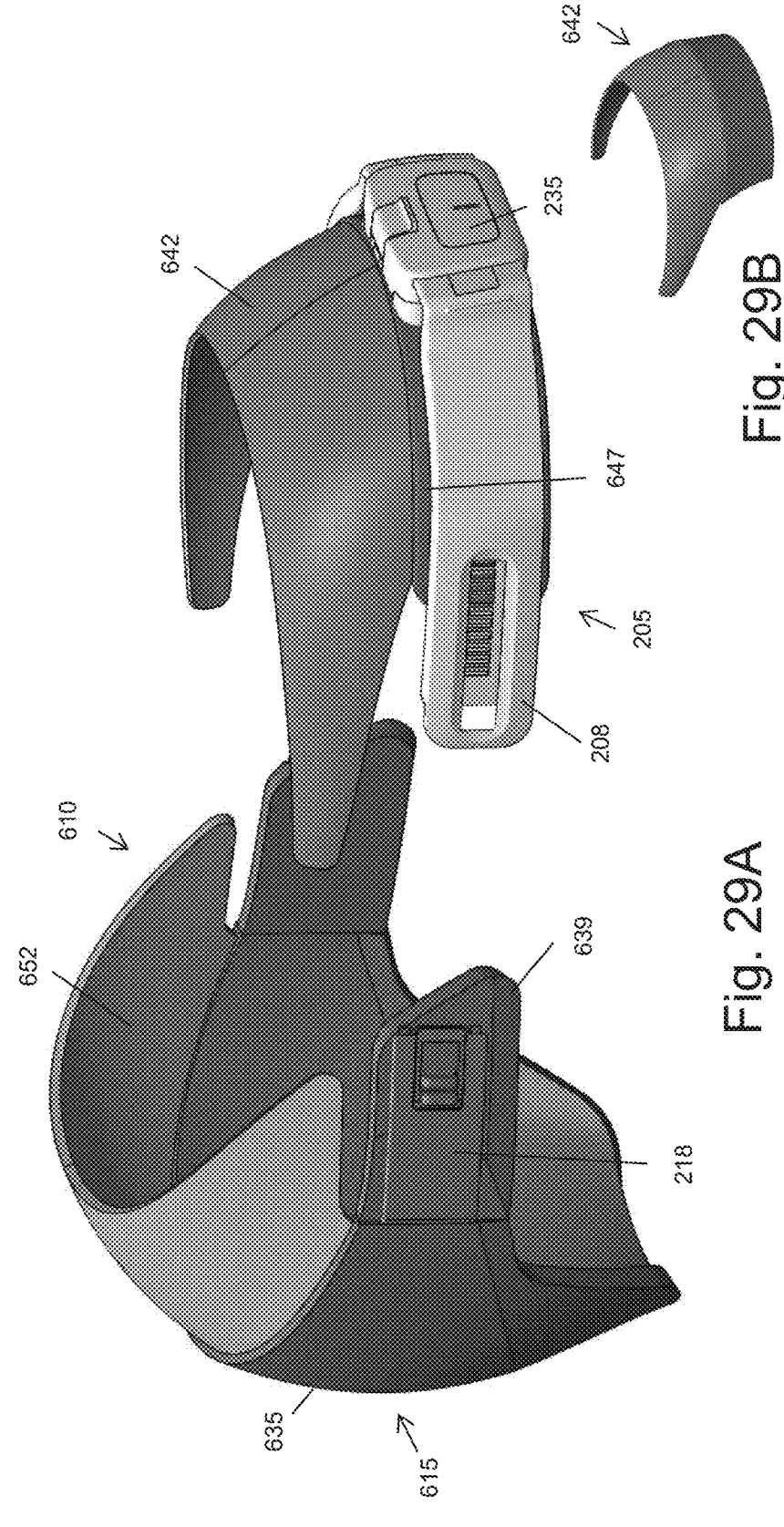
Figure 30:
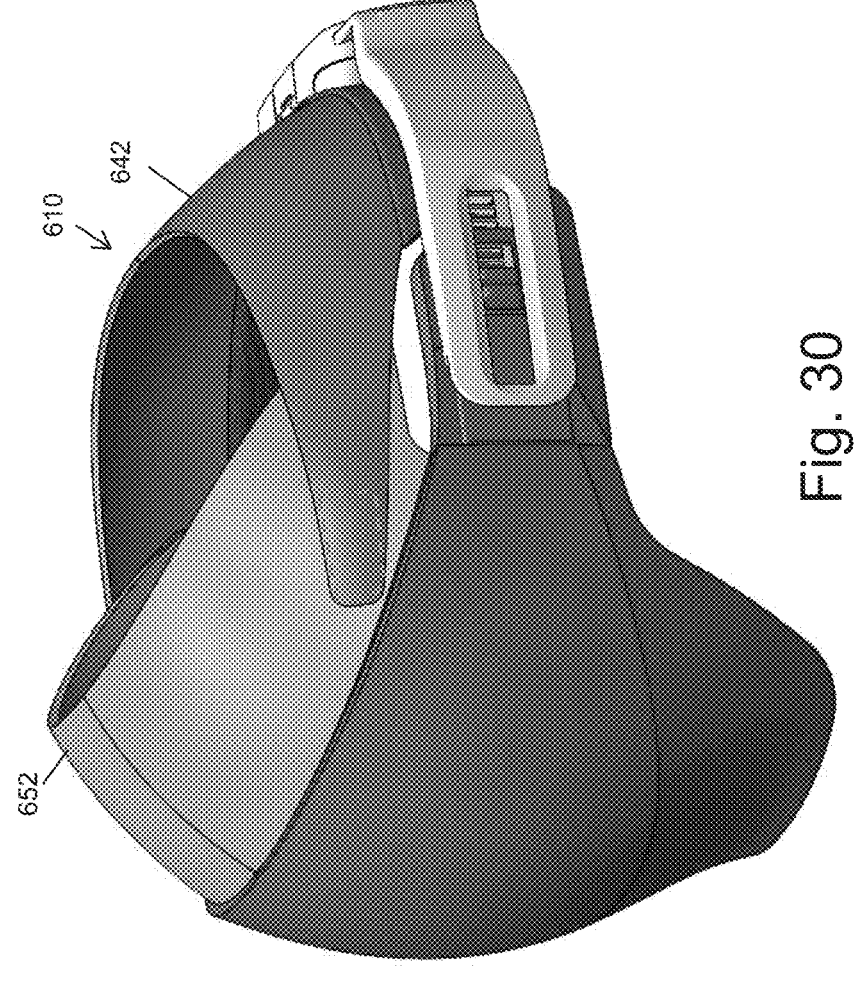
Figure 31:
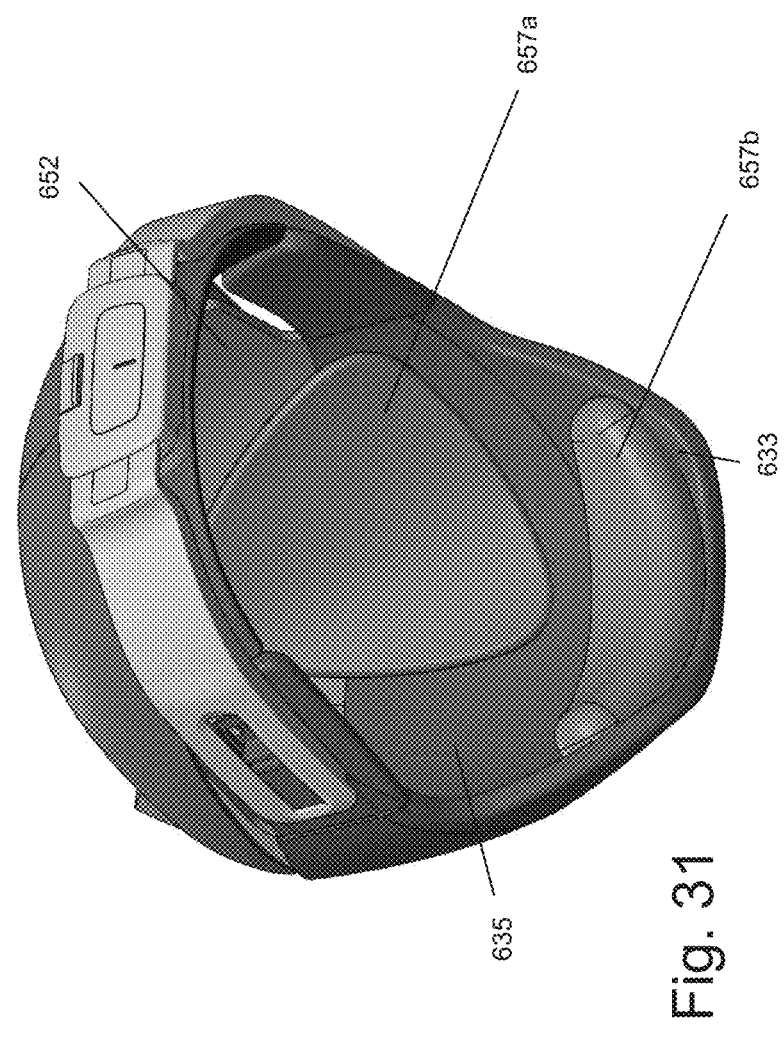
Figure 32:
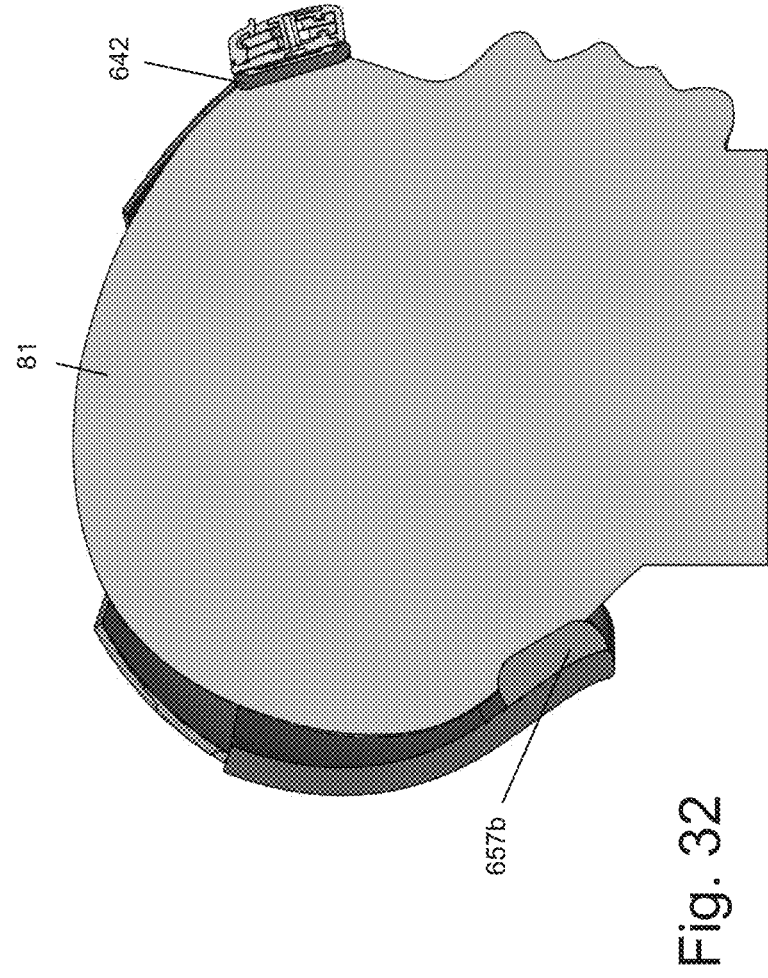
Figure 33:
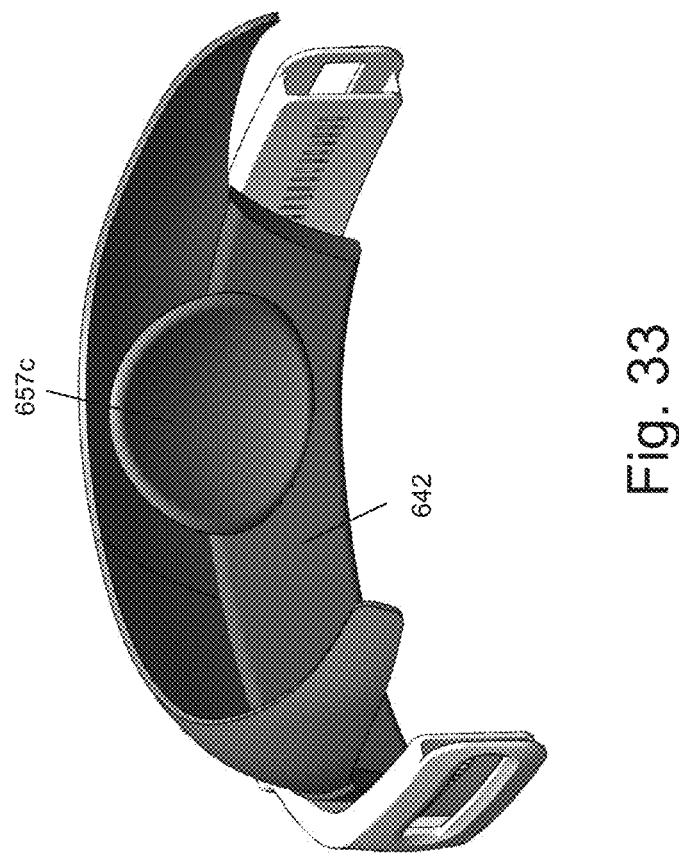
Figure 34:
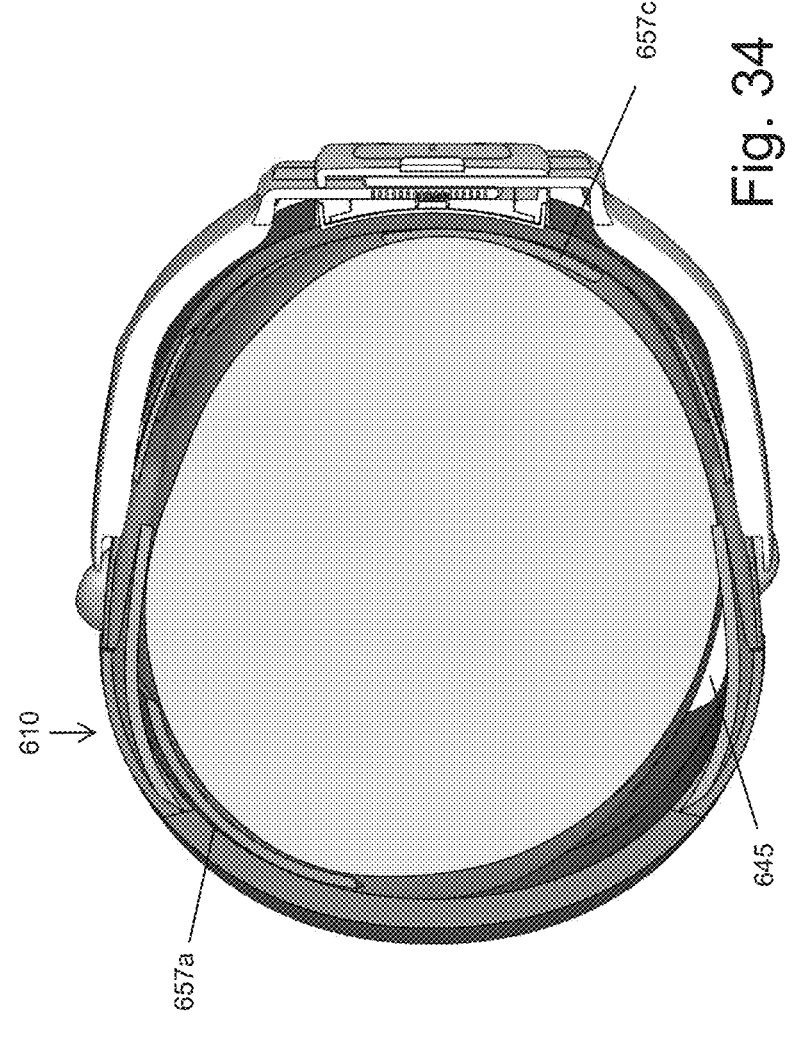

FIG. 19, showing elements of another embodiment of a lateral displacement limiting unit;

FIGS. 25A-D are a front perspective view, a side perspective view, a rear perspective view and a top perspective view, respectively, of a cranial orthosis based diagnostic product;

FIG. 26A is a top view of the orthosis of FIG. 25B;

FIG. 26B is a cross sectional view of the orthosis, cut along plane A-A of FIG. 26A;

FIG. 26C is a cross sectional view of the orthosis, cut along plane B-B of FIG. 26A;

FIG. 27 is a method for diagnosing and correcting a skull deformity;

FIGS. 28A and 28B are two schematic illustrations, respectively, of an operation performed by a microcontroller in conjunction with an orientation sensor and IMU to determine an instantaneous head position;

FIG. 29A is an exploded perspective view of another embodiment of a cranial orthosis;

FIG. 29B is a perspective view of an anterior securement enhancer used in conjunction with the orthosis of FIG. 29A;

FIG. 30 is a perspective view from above of the orthosis of FIG. 29A, when assembled;

FIG. 31 is a perspective posterior view from below of the orthosis of FIG. 29A when assembled, showing two attached pads;

FIG. 32 is a perspective cross sectional view of the orthosis of FIG. 31, showing elements thereof in contact with an infant's head;

FIG. 33 is a perspective anterior view of the anterior section of the orthosis of FIG. 30, showing an attached pad; and FIG. 34 is a top view of the orthosis of FIG. 30, showing two pads that are attached relative to a flattened occipital area.

DETAILED DESCRIPTION OF THE INVENTION

The cranial orthosis is a therapeutic headpiece that is adapted to encircle the skull of an infant suffering from positional plagiocephaly or brachycephaly or scaphocephaly and to induce cranial remodeling to achieve symmetry and adequate proportions, by providing passive protection to the circumferential outline of the infant's head. The headpiece will be coupled to the prominent areas, while leaving a gap in the flat area, in order to redirect the head growth. The cranial orthosis is adjustable to take into account the growth of the infant (in order to fit various shapes and size ranges of the infant's skull), and has a posterior section (the posterior section may also be rigid, flexible or spring-like) that is configured, in one embodiment, with one or more sagittally spaced arcuate pieces following the contour of a normal symmetric skull, as well as an anterior section that is securable with the posterior section and configured with a forehead engageable member.

According to one embodiment, the headpiece is devoid of any material connecting the anterior portion to the posterior portion along the crown of the skull to its vertex, and is therefore surprisingly light, significantly reducing its weight. The infant will be able to comfortably perform activities when lying on its stomach even though the headpiece is secured to the infant's cranium. According to another embodiment, the headpiece may include lightweight and soft material that will be added to the area along the crown of the skull, for padding to prevent pressure points and falling of orthosis to neck area.

Therapeutic Product

Figure 1:
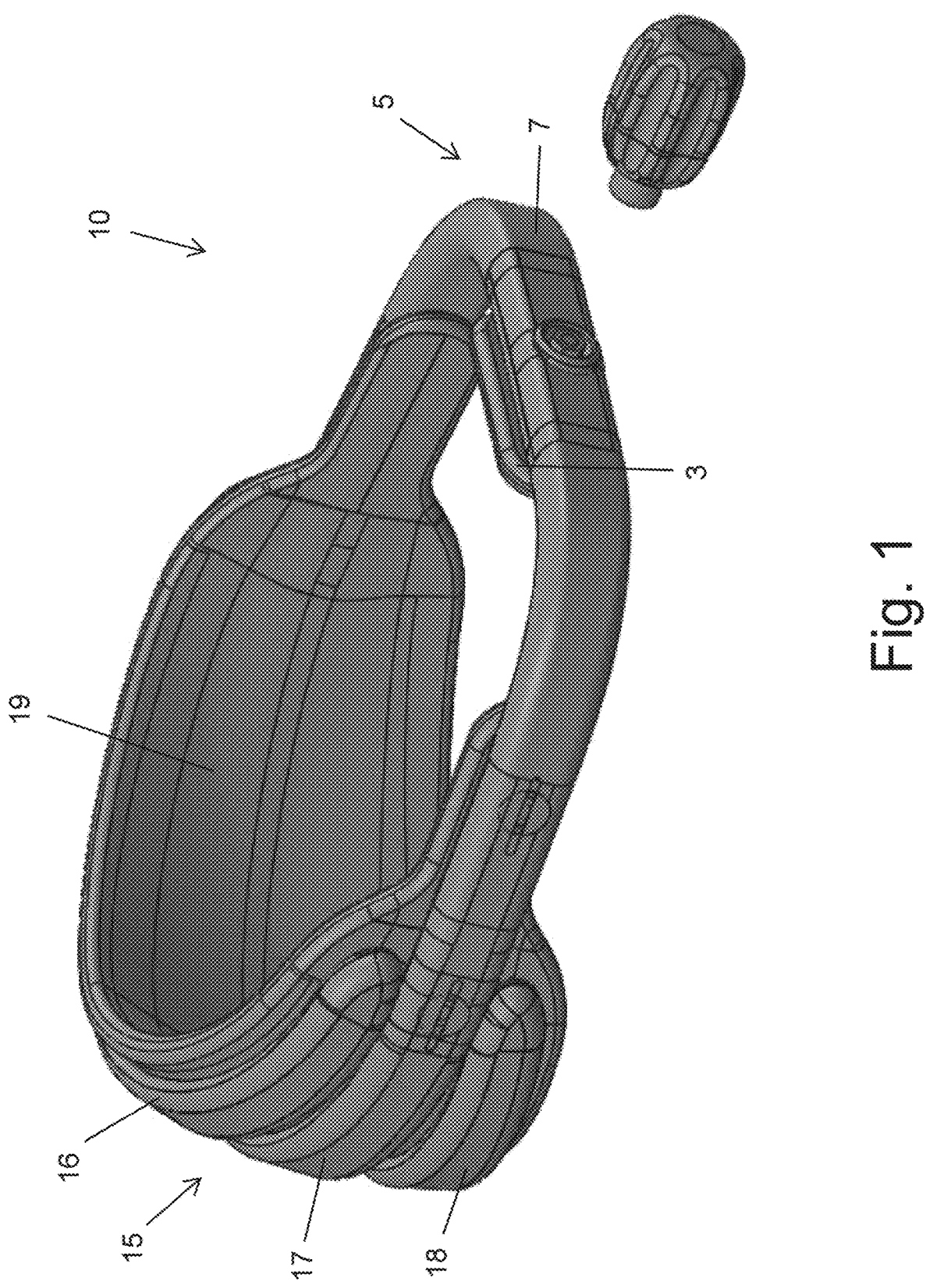
FIG. 1 is a perspective view of an embodiment of adjustable cranial orthosis, when assembled.

FIG. 1 illustrates an embodiment of adjustable cranial orthosis 10. Cranial orthosis 10 comprises anterior section 5 and posterior section 15.

Anterior section 5 is configured with a rounded U-shaped support frame 7 made from a structurally strong and relatively lightweight material, such as aluminium and rigid, or plastic material such as reinforced plastic material, and covered by a protective sheath, such as made of a hard plastic for the center piece and a textile or other soft/flexible material for the side parts. As support frame 7 is intended not to be in contact neither with the forehead nor with the temples of the infant, forehead engageable member 3 provided with padding is attached to the posterior side of the laterally extending portion of support frame 7. These lightweight parts (that may be covered in a soft fabric at all stages of use) are adjustable, and are comprised of 2 L-shaped parts, that glide over each other for adjustability.

Alternatively, U-shaped anterior section 5 may be configured as a flexible strap, which may include padding material or elements that are contactable with landmarks associated with the forehead of the infant.

Posterior section 15 may have three rigid arcuate pieces 16-18, for example made of a hard and lightweight, yet flexible, plastic material such as nylon, polypropylene, High-density polyethylene (HDPE), acetyl and polycarbonate, and a padding member 19 attached to the inner side of arcuate pieces 16-18 for increased comfort when cranial orthosis 10 is worn. Alternatively, the plastic material may be combined with spring steel strips. Intermediate arcuate piece 17 anteriorly protrudes from, and is sagittally interposed between, arcuate pieces 16 and 18. The padding member may also be designed in such a structure and shape, so as to enable adjustment to prevent movement and slipping of device towards the neck. It may be attached also to the anterior section and be adjustable together with anterior and posterior sections. The padding may have detachable pockets or other means for attaching or detaching spacer pads or cushions, to improve stability, fit and comfort, and also to provide a desired gap between the posterior section and a flattened area of the head.

It will be appreciated that the structure of the arcuate pieces is suitable for any embodiment described herein.

Intermediate arcuate piece 17 has two laterally separated anteroposterior portions, each of which is coupled and collinear with a corresponding anteroposterior portion of the support frame sheath, and an arcuate portion extending between the two anteroposterior portions. Support frame 7 and intermediate arcuate piece 17 are preferably covered with a common protective lining.

It will be appreciated that posterior section 15 may have any other number of arcuate pieces.

Figure 2:
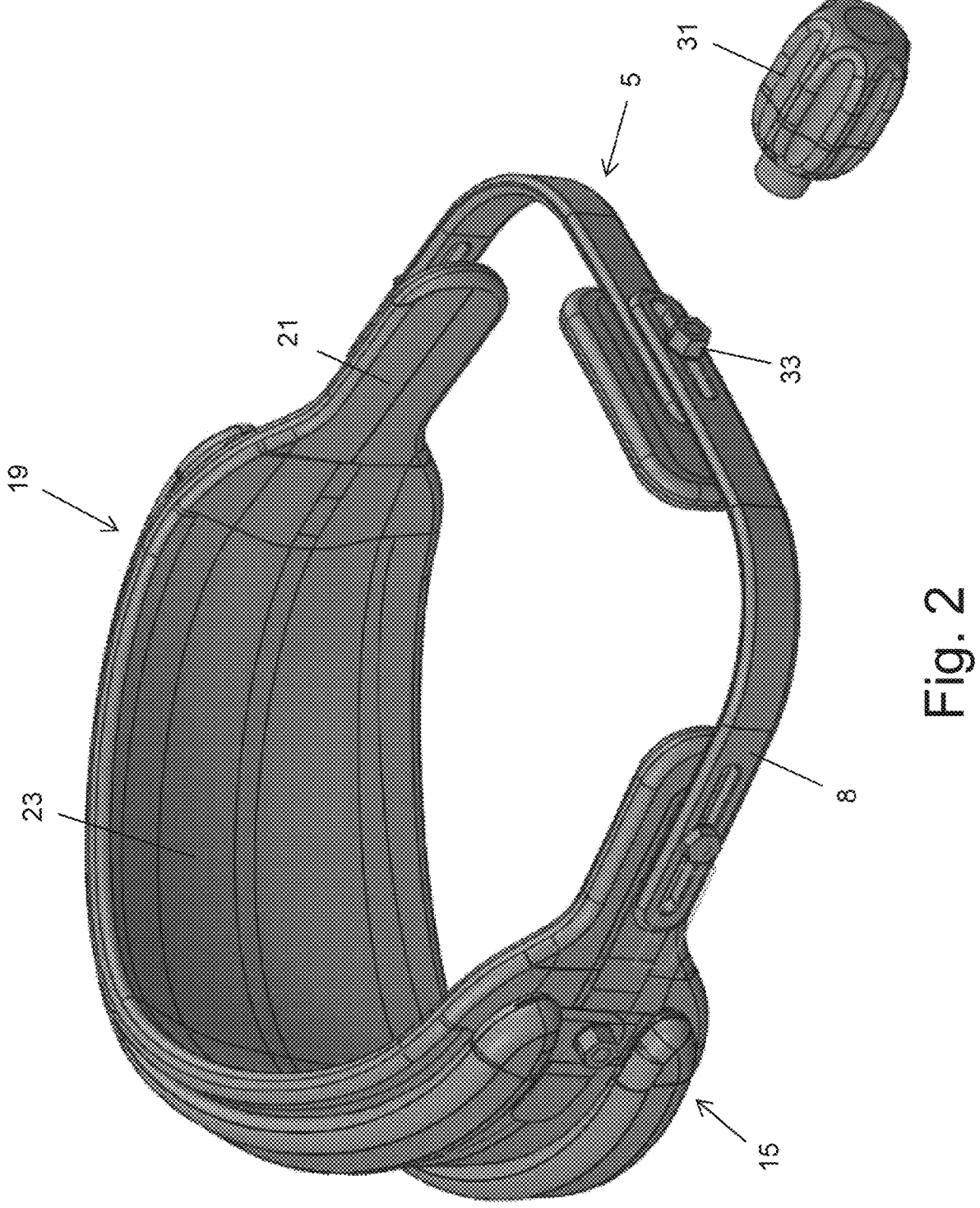
FIG. 2 is a perspective view of the adjustable cranial orthosis of FIG. 1, when an intermediate arcuate piece of the posterior section and a protective sheath of the anterior section are removed.

The configuration of padding member 19 is shown in FIG. 2. Padding member 19 has two relatively narrow temple engaging portions 21 that are attached to a corresponding anteroposterior portion 8 of the support frame of anterior section 5 and that slightly protrude superiorly therefrom. An arcuate occipital portion 23 of increased width extends continuously from one temple engaging portion 21 to another, and is adapted to engage the back of the head from the vertex at the top of the head to the nape of the neck proximate to the nuchal ridge, although it is primarily adapted to induce cranial remodeling in response to the presence of positional plagiocephaly in an occipital area. Padding member 19 may be made of hypoallergenic, biocompatible, and breathable foam that is soft and pleasant when contacted by the infant.

Also shown is an adjustment key 31 for tightening a nut 33, or other suitable fastener, on anterior section 5 or on posterior section 15. The key may be designed to be unintimidating and may be made smaller and integral in the orthosis. The adjustment mechanism may be an integrated mechanism that will enable adjustment of the width and possibly the length of the device, by turning a built in mechanism and a knob, such as in a molding helmet.

Figure 3:
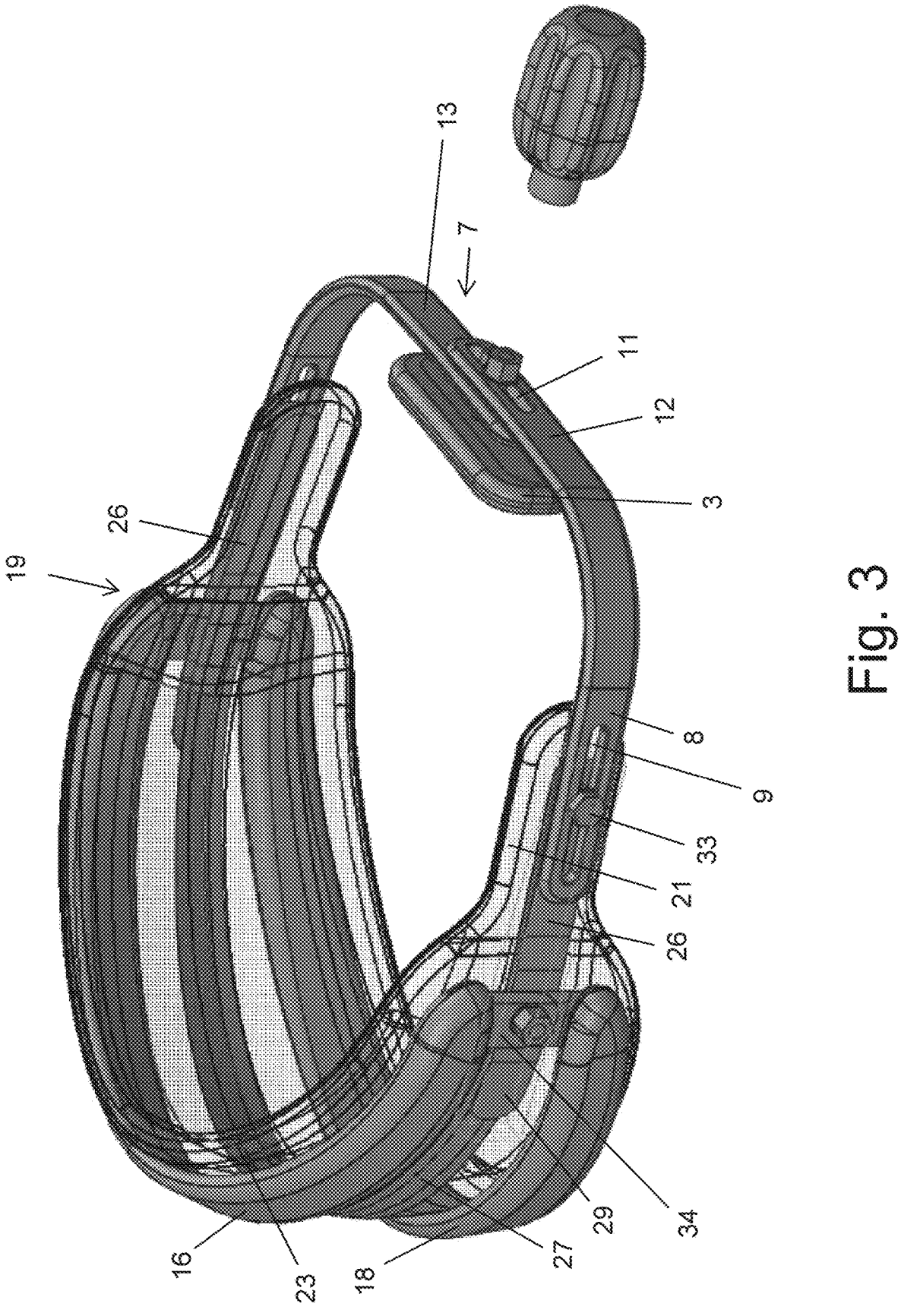
FIG. 3 is a perspective view of the adjustable cranial orthosis of FIG. 1, when an intermediate arcuate piece of the posterior section and a protective sheath of the anterior section are removed and the padding member is shown to be transparent.

As shown in FIG. 3, an insert 26, e.g. an elliptical and planar insert made of steel or may have a plastic structure and possibly made from a reinforced plastic. The insert 26 is integrally formed with padding member 19, and extends anteroposteriorly within both temple engaging portion 21 and occipital portion 23 and is of substantially the same height as anteroposterior portion 8 of support frame 7. A screw connected to insert 26, such as by welding, passes through a groove 9 provided in anteroposterior portion 8 of support frame 7 and is used for adjustment purposes by securing nut 33 threadedly fastened with the screw. It will be appreciated that other adjustment means may be employed as well.

Support frame 7 is shown to have two laterally extending portions 12 and 13, each of which formed with a groove 11. The two laterally extending portions 12 and 13 are adjustably connected to each other by a screw and nut arrangement cooperating with the grooves 11. The screw may be connected to a steel insert integrally formed in forehead engageable member 3. Alternatively, a linear rail & cog wheel mechanism with a knob may be used to enable a symmetrical adjustment movement of portions 12 13.

A sagittally extending and narrow support appendage 34, which may be perpendicular to insert 26, may be fixedly attached, such as by a screw and nut arrangement, to the outer side of insert 26. Appendage 34, when protruding beyond insert 26, is used for facilitating angular displacement of arcuate pieces 16 and 18. A curved brace (not shown) pivotally connected to a corresponding protruding extremity of appendage 34 in such a way that the brace is capable of undergoing restricted rotation is inserted within, and attached to, the arcuate piece. Thus the arcuate piece is able to be fixed in position to provide location-specific support to the infant after the brace is pivoted.

Padding member 19 is shown to be configured with a compressible backing element 27 that slightly protrudes outwardly from occipital portion 23 and that is positioned between arcuate pieces 16 and 18. Padding may be easily removed and attached for washing or fitting a thicker padding. Alternatively, the padding may have pockets for adding additional padding selectively. These pockets may be used to add pads in order to fill unwanted gaps and improve stability and reproducibility/repetitiveness for repositioning after washing.

Backing element 27 is used to support the intermediate arcuate piece and follows the arcuate contour of occipital portion 23. Since backing element 27 curves together with occipital portion 23 close to the interface with temple engaging portion 21, a posterior portion 29 of the substantially planar anteroposteriorly extending insert 26 that protrudes from appendage 34 is slightly spaced from the curved backing element 27. The spacing between backing element 27 and posterior portion 29 is sufficient for the insertion of a wall of the hollowed intermediate arcuate piece therebetween, when being coupled with posterior portion 29.

Various possibilities of adjusting cranial orthosis 10 are schematically illustrated in FIGS. 4A-B. Widthwise adjustment mechanism will enable symmetrical change on both the left and right side of the device. Adjustment of the width of the device changes the curvature of the arcuated pieces, which are flexible in order to enable the curvature and strong enough to hold the weight of the head.

Arcuate pieces 16 and 18 are able to be angularly adjusted about the transversal axis by which a curved brace is pivotally connected to a sagittally extending appendage, as indicated by arrow 32. The rigid arcuate pieces that are secured to the round back of the head prevent contact between a flattened occipital area and the flat surface on top of which the infant is lying. As the cause of the cranial deformity is averted, unrestricted occipital growth in response to rapid brain growth is made possible. Thus the cranial bones are pushed outward while the infant's head rests in the concave space defined by the arcuate pieces 16-18 and the padding member until the normal rounded cranium structure is achieved.

The length of the orthosis is able to be adjusted by displacing a temple engaging portion 21 of the padding member relative to the corresponding anteroposterior portion 8 of the support frame and securing the nut, as indicated by arrow 34. The width of the orthosis is able to be adjusted by displacing the two laterally extending portions of the support frame relative to one another and securing the nut, as indicated by arrow 36. Since the dimensions of the cranium change during periods of occipital growth, the length and width of the orthosis generally have to be continuously adjusted to ensure suitable securement of the anterior and posterior portions.

FIGS. 8-13 illustrate another embodiment of a cranial orthosis 80, which facilitates adjustment in response to both lengthwise and widthwise skull growth.

As shown in FIG. 8, cranial orthosis 80 comprises anterior section 85 and posterior section 105 that are releasably coupled together and that are adapted to be secured to the skull 81 of an infant. Each of anterior section 85 and posterior section 105 comprises a support frame, a protective sheath by which the support frame is enclosed, and a padding element with which the protective sheath is engaged. The type of material from which each of the elements is made may be similar to that of cranial orthosis 10 of FIG. 1, with the exception of the posterior support frame, which is structurally strong and flexible to at least a certain extent, for example made of plastic material such as polypropylene, HDPE, acetyl and polycarbonate.

Posterior section 105 comprises two arcuate pieces 101 and 102 that are angularly spaced from each other and are adapted to follow, and to be continuously secured to, the rounded contour of skull 81, which is presently symmetrically shaped or intended to be symmetrically shaped following the unrestricted occipital growth that is able to be induced by cranial orthosis 80. At each lateral side of skull 81, the two arcuate pieces 101 and 102 combine together at interface portion 107 to define a Y-shaped structure. Interface portion 107 in turn extends continuously to the corresponding anteroposterior portion 108.

Anteroposterior portion 108 is formed with an aperture, e.g. elliptically shaped, a border 109 of which serving to limit translational displacement of a protuberance 104 connected to a support frame insert 103, which is visible through the aperture. Protuberance 104 is shown to be positioned at the extreme anterior end of border 109 corresponding to a minimal orthosis length. As skull 81 becomes enlarged, protuberance 104 and insert 103 are displaced posteriorly to accommodate the enlarged skull dimensions, until arcuate pieces 101 and 102 are once again secured to the skull, In FIG. 9, protuberance 104 is shown to be positioned at the extreme posterior end of border 109, causing posterior section 105 to become spaced from skull 81.

FIG. 10A illustrates an exploded view of orthosis 80, including the anterior support frame 93, the anterior protective sheath 94, the anterior padding element 96, the posterior support frame 112, the posterior protective sheath 114, and the posterior padding element 116.

Anterior padding element 96 and posterior padding element 116 are shown to be in close proximity to each other, defining the concave space 111 within which the infant's skull is positionable in order to undergo cranial remodeling. The inner face of both anterior padding element 96 and posterior padding element 116 facing towards concave space 111 is completely smooth to increase comfort of the infant. The outer face of anterior padding element 96 and posterior padding element 116 facing away from concave space 111 is each formed with upper and lower outwardly protruding portions that facilitate suitable positioning of the corresponding support frame or the corresponding enclosing protective sheath. Posterior padding element 116 may comprise an upper lacing 87A and a lower lacing 87B for fastening the padding element 116 to the infant's head. Each lacing is terminated with a fixation element 95 (such as a hook or a Velcro fastener strap), for fixating each lacing edge to the external surface of the padding element 116.

FIG. 10B illustrates the posterior protective sheath 114, with an incision 119 that allows inserting the posterior support frame 112, into the posterior protective sheath 114, such that it will wrapped before attachment to the posterior padding element 116.

As shown for example in FIG. 11, arcuate pieces 91 and 92 of the posterior support frame are positioned above and below, respectively, lower protruding portion 118 of posterior padding element 116 while generally being in abutting relation therewith. While upper protruding portion 117 of posterior padding element 116 extends throughout the circumferential length of the latter, lower protruding portion 118 extends only along a limited length of posterior padding element 116 so as not to interfere with the positioning of interface portion 107 of the posterior support frame.

Anterior support frame 93 is U-shaped and configured with rectilinear forehead engageable member 88 from which anteriorly protrudes a sensor module 142 and with two opposed L-shaped elements 89A and 89B that are each slidably and adjustably introducible into corresponding sockets 86A and 86B, respectively, of forehead engageable member 88 for widthwise adjustment. The laterally extending portion of each of the two L-shaped elements 89A and 89B is securable to forehead engageable member 88, for example with thin securing element 123 (FIG. 12). The anteroposterior portion 84 of each L-shaped element 89 is formed with an aperture 83 that permits displacement of protuberance 104. L-shaped elements 89A and 89B are engaged by a cog-wheel 89C, such any displacement of one of them in its corresponding socket will cause movement of the other L-shaped element in the opposite direction, as shown in FIG. 12 (so as to ensure a symmetrical configuration of the U-shaped anterior section 5).

As shown in FIG. 12, each anterior anteroposterior portion 84 comprises a thin hollow chamber having opposed walls 127 and 128. The spacing between walls 127 and 128 is sufficiently large to receive and secure a posterior support frame insert 103. Posterior support frame insert 103 is introduced via a posterior opening of the corresponding anteroposterior portion 84. When insert 103 is inserted within anteroposterior portion 84 to a maximum extent as shown, the circumferential length of posterior section 105 able to be secured to the infant's skull, particularly arcuate piece 92, is limited, and therefore resists expansion of the infant's skull.

After insert 103 has been introduced into the corresponding anteroposterior portion 84, protuberance 104 is connected to the insert, for example threadedly connected via a threaded aperture formed in the insert, and is caused to be engaged with a border 129 of an inner aperture formed in wall 128 and thereby being prevented from being displaced. The engagement with border 129 is sufficiently strong so that anterior section 85 and posterior section 105 are able to remain engaged together even when not secured to an infant's skull, as shown in FIG. 11.

Once protuberance 104 is slightly loosened, it is free to be displaced anteroposteriorly along the space between borders 109 and 129, together with insert 103.

Protuberance 104 may be connected to insert 103 by other means well known to a person skilled in the art.

Anterior protective sheath 94 and posterior protective sheath 114 are able to introduced over anterior support frame 93 and posterior support frame 112, respectively, through bottom and/or upper slits formed in each protective sheath, after anterior section 85 and posterior section 105 have been coupled together, or alternatively prior to being coupled together. Anterior protective sheath 94 and posterior protective sheath 114 are able to be coupled together in conjunction with means well known to a person skilled in the art when one hollow end member 131 of one of them is inserted within a hollow end member of the other.

FIG. 13A illustrates posterior section 105 when retracted from anterior section 85 relative to the position shown in FIG. 12, following displacement of the protuberance. Only a fraction of the length of insert 103 is received in anteroposterior portion 84, and therefore interface portion 107 and the remaining length of insert 103 are unrestricted. The circumferential length of posterior section 105 that is able to be secured to the infant's skull is significantly increased relative to that shown in FIG. 12 by virtue of the unrestricted insert 103, and therefore supports expansion of the infant's skull both in a lengthwise and widthwise direction.

FIG. 13B illustrates posterior section of FIG. 13A, following further displacement of the two L-shaped elements 89A and 89B laterally, with respect to each other, so as to gain extra width (in addition to the extra length gained as illustrated in FIG. 13A) to receive a larger infant's head.

FIG. 14 illustrates another embodiment of an adjustable cranial orthosis, generally indicated by numeral 210. Cranial orthosis 210 comprises a headpiece 207 to which is operatively connected right and left lengthwise adjustment mechanisms 225 and a widthwise adjustment mechanism 235 housed within a forehead engageable member, which may be configured with one or more planar surfaces. Headpiece 207 comprises U-shaped anterior section 205 fitted with widthwise adjustment mechanism 235 and posterior section 215 that has three arcuate pieces 196-198. Headpiece 207 may be covered completely or partially with a protective sheath.

As shown in FIG. 15, each lengthwise adjustment mechanism 225 comprises an anteroposterior portion 208 provided with anterior section 205 and an anteroposterior portion 218 provided with posterior section 215 that are releasably coupled together. Each lengthwise adjustment mechanism 225 is adapted to differentially and accurately adjust the length of the corresponding side of the headpiece as well as to ensure that the coupled anteroposterior portions 208 and 218 will not be disengaged and will continue to collectively define the length of the corresponding headpiece side.

Anteroposterior portion 208 is bifurcated to define inner and outer surfaces. The inner surface is a temple-engaging surface 201 formed with a plurality of sagittally extending teeth 203 facing outer surface 209 to provide a rack. Teeth 203 are all inclined in one direction (see FIGS. 18A-B) and are formed as ratchet teeth, each tooth 203 having a sliding surface inclined relative to an advance direction and a stop surface facing in a setback direction which is opposite to the advance direction to intersect two adjacent sliding surfaces. The stop surface defines the depth of a tooth 203. Outer surface 209 is formed with an aperture 211, e.g. elliptical, and may be imprinted with adjusted length indicating indicia 214.

Anteroposterior portion 218 is fitted with a resilient clamping unit 221 adapted to cooperate with the rack teeth 203 to ensure that the clamping force applied on the head of an infant when the length-adjusted anteroposterior portions 208 and 218 remain coupled together during a length adjustment operation will not be excessive and injurious to the infant. A length setting handle 226 and a decoupling initiating handle 248 of resilient clamping unit 221 protrude through aperture 211 when anteroposterior portions 208 and 218 are coupled together as shown in FIG. 14.

As shown in FIG. 16, resilient clamping unit 221 comprises inwardly facing elastomeric ring support 224 that protrudes from anteroposterior portion 218, pawl holder 232 that is linearly displaceable along anteroposterior portion 218, pivotal pawl assembly 243 receivable within pawl holder 232, and rectangular elastomeric ring 252 resiliently secured to pawl holder 232 and to inwardly facing ring support 224.

Anteroposterior portion 218 is configured with a recess 216 having parallel superior and inferior edges that is recessed from the inner face 219 of portion 218 to expose its outer face 222 from which ring support 224 inwardly protrudes. Outer face 222 is formed with a U-shaped aperture 223. Elongated regions 219a-b of inner face 219 bordering recess 216 and elongated regions 222a-b of outer face 222 bordering aperture 223 that extend to the anterior edge 213 of anteroposterior portion 218 are rendered flexible by virtue of the unattached regions bordering aperture 223. The posterior edge 224 of aperture 223 serves to limit the posterior displacement of length setting handle 226 upon being contacted thereby.

Ring support 224 may be configured with an inner surface, e.g. arcuate, which is parallel to face 222, and with a narrow supporting surface 224a that is substantially perpendicular to face 222. Supporting surface 224a of ring support 224 is adapted to be in abutting relation with the posterior edge 254 of elastomeric ring 252, as shown in FIGS. 17A-B.

Anteroposterior portion 218 also has a superior surface 227 and an inferior surface 217, each extending between corresponding regions of inner face 219 bordering recess 216 and of outer face 222 bordering aperture 223. A superior rail 204 is defined by superior surface 227, superior inner face region 219a and superior outer face region 222a. An inferior rail 206 is defined by inferior surface 217, inferior inner face region 219b and inferior outer face region 222b. Superior rail 204 and inferior rail 206 are used to facilitate the linear displacement of pawl holder 232.

Pawl holder 232 has two parallel sagittally extending border elements 228a-b, and mutually parallel superior surface 229 and inferior surface 231 anteroposteriorly extending between, and wider than, border elements 228a-b to define, at each of the inner and outer pawl holder faces, a rectangular coplanar border. Within the central opening of the border are provided an integral posteriorly positioned wall 234 slightly spaced from the inner face of the border and from which length setting handle 226 outwardly protrudes, and an anteriorly positioned void space 236. A pin support surface 233 positioned between the two borders slightly protrudes from inferior surface 231 at a region anterior to wall 234. One or more guiding elements 238 sized for insertion within and slidable displacement along superior rail 204 protrude from superior surface 229, and one or more guiding elements 239 sized for insertion within and slidable displacement along inferior rail 206 protrude inferiorly from inferior surface 231.

Linear displacement of pawl holder 232 along superior rail 204 and inferior rail 206 may be limited by a ramped stopper 212 protruding from the inferior surface 217 of anteroposterior portion 218 upon contacting a discontinuity in inferior surface 231 of pawl holder 231 or any other suitable surface. Pawl holder 232 is posteriorly positionable relative to stopper 212 upon flexing superior rail 204 and inferior rail 206, and is separable from anteroposterior portion 218 by manipulation of a dedicated implement in the proximity of stopper 212 and the subsequent flexing of superior rail 204 and inferior rail 206.

A narrow support 237 for the anterior edge 253 of elastomeric ring 252 protrudes outwardly from border element 228a, and is configured with a recessed portion for receiving anterior ring edge 253. A gap is defined between elastomeric ring support 237 and each of superior surface 229 and inferior surface 231 to accommodate the extension of the superior edge 257 and inferior edge 258 of elastomeric ring 252 between its anterior edge 253 and posterior edge 254.

Pawl assembly 243, which has a length substantially equal to the central opening of the pawl holder border and may be made of rigid material, has an anterior pawl bearing wall 241 that is substantially perpendicular to decoupling initiating handle 248 and a posterior plastically deformable wall 244, similar in function to a leaf spring, that is slightly angularly spaced from wall 241. For example, plastically deformable wall 244 is angularly spaced from pawl bearing wall 241 by an angle of approximately 15 degrees and from decoupling initiating handle 248 by an angle of approximately 105 degrees. A pawl 246 of right-triangular configuration which is complementary to each rack tooth 203 (FIG. 15) protrudes from the inner face of wall 241 such that its vertex coincides with the anterior end of wall 241, or is slightly posteriorly spaced therefrom, and one of the sides defining its largest width is facing the posterior direction. While pawl bearing wall 241 is relatively thick to load pawl 246 into engagement with one of the rack teeth, plastically deformable wall 244 is relatively thin and rendered sufficient resilient to absorb a spring force when set in pressing abutting relation with temple-engaging surface 201 of anteroposterior portion 208 (FIG. 15). A single pin 249 is receivable in the aligned holes 242 formed in pawl holder superior surface 229 and pin support surface 233, and in the through-hole formed within wall 241 proximate to the junction of walls 241 and 244, to facilitate pivotal displacement of pawl holder 243.

FIGS. 17A-B illustrate resilient clamping unit 221 when assembled. Pawl holder 232 is retracted in FIG. 17A and is extended in FIG. 17B, its displacement when extended being limited by stopper 212 (FIG. 16). As pawl holder 232 is extended, rectangular ring 252 becomes stretched. Even when pawl holder 232 is extended and the head orientation of the infant user is changed such that the superior rail is downwardly facing, the pin by which pawl assembly 243 is pivotable remains enclosed by the superior rail and therefore is assured of not being dislodged from the aligned holes within which it is received.

FIGS. 18A-B illustrate lengthwise adjustment mechanism 225 when anteroposterior portion 208 is coupled with anteroposterior portion 218. Gap 202 between the inner surface 201 and outer surface 209 of anteroposterior portion 208 is dimensioned essentially with the same lateral dimension as the thickness of wall 220 of anteroposterior portion 218, between its inner face 219 and outer face 222, to urge pawl 246 into engagement with one of the rack teeth 203 by virtue of the contact between outer face 222 of anteroposterior portion 218 and outer surface 209 of anteroposterior portion 208.

After pawl holder 232 is advanced by suitable manipulation of length setting handle 226, pawl 246 is engaged with a tooth 203 that is more anteriorly positioned in FIG. 18B than in FIG. 18A. Since pawl assembly 243 is mounted within pawl holder 232 by means of pin 249, pawl assembly 243 is caused to be displaced anteriorly when an anteriorly directed initiating force is applied to length setting handle 226 protruding from pawl holder 232, such as by a finger. During anterior displacement of pawl assembly 243 in the advance direction, pawl 246 clicks from one rack tooth 203 to the next while advancing along the sliding surface 203a of each tooth. If an attempt is made to apply an initiating force onto length setting handle 226 in the setback direction, a stop surface 203b of each tooth 203 prevents displacement of pawl assembly 243 and of pawl holder 232 in this direction.

If for some reason it is desired to shorten the length of the headpiece, decoupling initiating handle 248 is manipulated by applying an initiating force thereto in the direction of length setting handle 226. Decoupling initiating handle 248, as well as the entire pawl assembly 243, is consequently caused to pivot about pin 249 so that pawl 246 will be decoupled from rack teeth 203 and pawl assembly 243 and pawl holder 232 will be free to be displaced in the posterior setback direction. While pawl assembly 243 is pivoted, in the clockwise direction according to the illustrated orientation, wall 244 is pressed against inner surface 201 of anteroposterior portion 208 and becomes plastically deformed, absorbing spring-like potential energy. Following cessation of the initiating force applied to decoupling initiating handle 248, the potential energy absorbed by wall 244 is released and pawl assembly 232 pivots in the opposite rotational direction to assume its original orientation at which pawl 246 is engaged with a tooth 203.

The lateral end of plastically deformable wall 244 may be configured with appendages 244a and 244b protruding sagittally from the superior and inferior surfaces, respectively, of pawl bearing wall 241. Appendages 244a and 244b ensure that plastically deformable wall 244 of pawl assembly 243 will contact uncompromised portions of temple-engaging surface 201 of anteroposterior portion 208 being superior and inferior, respectively, to the rack teeth 203 when pawl holder 232 is anteriorly displaced and will therefore not contact the rack teeth. Thus wear of the rack teeth that will retard anterior displacement of pawl holder 232 is advantageously avoided.

The clamping force applied onto the head of the infant when anteroposterior portions 208 and 218 are coupled together through the intervention of pawl 246 is anticipated to increase as pawl holder 232 is advanced and widthwise adjustment mechanism 235 (FIG. 14) is brought closer to posterior section 215. By use of a resilient element, such as rectangular elastomeric ring 252 or a spring, which is connected between pawl holder 232 and anteroposterior portion 218, over tension is able to be prevented by advantageously decreasing the clamping force through the indirect mediation of the resilient element. During advance of pawl holder 232, the resilient element is initially relatively slack to reduce the sensed clamping force. Rectangular ring 252 also has significant utility in that the compressive force applied thereby onto pawl holder 232 and anteroposterior portion 218 serves to draw the forehead engageable member in which widthwise adjustment mechanism 235 is housed into contact with the forehead of the infant undergoing cranial remodeling. When the infant is in a supine position and the posterior section of the headpiece is pressed downwards by a rounded occipital area of the infant, the forehead engageable member would be separated from the forehead without the assistance provided by the resilient element that urges the forehead engageable member into engagement with the forehead.

FIG. 19 illustrates assembled anterior section 205 that is fitted with the widthwise adjustment mechanism according to one embodiment for ensuring that right and left anteroposterior portions will be symmetrically positioned. As shown, anterior section 205 comprises right L-shaped piece 264 that includes right anteroposterior portion 208R, planar anterior portion 266 and connecting portion 268 interfacing between portions 208R and 266 which may be curved, left L-shaped piece 274 that includes left anteroposterior portion 208L, planar posterior portion 276 and connecting portion 278 interfacing between portions 208L and 276 which may be curved, bifurcated widthwise adjustment mechanism housing member 282 within an interior of which planar portions 266 and 276 are introducible and adjustably displaceable, and pivotal locking handle 288 that is securable with housing member 282. A functional or esthetic covering 287 may be coupled with the anterior surface 285 of housing member 282, such as by a press fit. Superior to covering 287 is formed an aperture 291 (FIG. 20) within anterior surface 285 for use in securing locking handle 288. A forehead engageable member may be defined by the anterior housing member 282 and a rigid posterior housing member coupled therewith, such as secondary housing member 293 shown in FIG. 20 that is abuttable with the forehead of the infant. Alternatively, a padding element attached to, or in abutment with, the posterior housing member is contactable with the forehead of the infant. An orientation sensor may be housed within the forehead engageable member or mounted externally thereto.

FIG. 20 illustrates anterior section 205 when exploded and the widthwise adjustment mechanism 235 that is enclosable by housing member 282. As shown, widthwise adjustment mechanism 235 comprises a pinion 262 that is rotatably mounted by pin 263 within seat 286 formed in secondary housing member 293 coupled with housing member 282. Secondary housing member 293 may be considerably thinner than housing member 282.

Coupling elements 297 protruding from the superior surface 289 of housing member 282 are adapted to be coupled with corresponding coupling elements 306 protruding from the superior surface 303 of secondary housing member 293. A support surface 313 is interposed between opposed coupling elements 306 of secondary housing member 293. When anterior housing member 282 and posterior secondary housing member 293 are coupled together, support surface 313 is positioned in abutting relation with the coupling elements and the superior surface 289 of housing member 282 may overlie the superior surface 303 of secondary housing member 293.

Anterior portion 266 is formed with an elliptical aperture 268 having substantially parallel superior 267 and inferior 269 straight edges arranged such that superior edge 267 is uncompromised and inferior edge 269 is formed with a plurality of evenly spaced superiorly pointing teeth. Posterior portion 276 is formed with an elliptical aperture 278 having substantially parallel superior 277 and inferior 279 straight edges arranged such that inferior edge 279 is uncompromised and superior edge 277 is formed with a plurality of evenly spaced inferiorly pointing teeth. The outer face of posterior portion 276 may be imprinted with adjusted width indicating indicia 284. The superior edge 281 of posterior portion 276 is formed with a plurality of evenly spaced teeth 283 adapted to be coupled with locking handle 288. Pinion 262 is intermeshed with both toothed edge 269 of anterior portion 266 and toothed edge 277 of posterior portion 276.

FIGS. 21A-B illustrate anterior section 205 when set to two different widths, after pinion 262 has been rotated to linearly drive toothed edge 269 of anterior portion 266 and toothed edge 277 of posterior portion 276 simultaneously.

As shown in FIGS. 22A-B, locking handle 288 comprises a thickened main surface 292 from each lateral end 294 of which a corresponding pivot pin 296 extends, a catch bearing surface 301 substantially perpendicular to, and thinner than, main surface 292, a curved surface 307 interconnecting main surface 292 and catch bearing surface 301 and adapted to abut the interface between anterior surface 285 and superior surface 289 of housing member 282, and a narrow handle element 309 angularly spaced from catch bearing surface 301 and extending away from main surface 292. Pivot pins 296 are rotatably mounted in corresponding seats each defined by a pair of coupling elements 297 and 306 that are coupled together.

A plurality of evenly spaced securing teeth 317, e.g. of triangular cross section, protrude from main surface 292, and are angularly spaced from teeth 283 formed in the superior edge 281 of posterior portion 276 when locking handle 288 is set to the unlocked position shown in FIG. 22B. A laterally extending catch 327 protruding proximate to the pivot pins from the face of main surface 292 that is opposite to the face from which teeth 317 protrude is introducible within aperture 316 formed in support surface 313 (FIG. 20) to assist in retaining locking handle 288 in the unlocked position. Teeth 317 of locking handle 288 are adapted to be secured between adjacent teeth 283 of posterior portion 276 when locking handle 288 is pivoted to the locked position shown in FIG. 22C by which additional lateral displacement of posterior portions 266 and 276 is prevented. A catch 321 protruding from surface 301 is securable within aperture 291 formed in anterior surface 285 of housing member 282 when locking handle 288 is set to the locked position.

FIGS. 23A-B illustrate a lateral displacement limiting unit 345 that is operable in conjunction with widthwise adjustment mechanism 235. Lateral displacement limiting unit 345 is configured with an elongated recess 349, e.g. elliptically shaped, which is recessed within a selected region of planar posterior portion 276 of left L-shaped piece 274 shown to be inferior to inferior uncompromised edge 279 of aperture 278. A plurality of laterally spaced threaded holes 343 sagittally aligned with recess 349 are formed in secondary housing member 293. A hole 343 closer to right L-shaped piece 264 is used when a smaller widthwise dimension is desired, and a hole closer to left L-shaped piece 274 is used when a larger widthwise dimension is desired. A health practitioner such as a physician sets a limit of lateral displacement limiting unit 345 by threadedly engaging small screw 341, e.g. having a length of 2 mm, into a selected hole 343 whose relative location serves to prevent application of an excessive widthwise clamping force onto the skull. According to this arrangement, screw 341 is sufficiently threadedly engaged with the selected hole 343 so as to be fixed in place while being slightly spaced from the solid wall region of posterior portion 276 that is delimited by the peripheral edge of recess 349. Since screw 341 is spaced from the solid posterior portion 276, anterior portion 266 and posterior portion 276 are able to be freely laterally displaced by widthwise adjustment mechanism 235. If, however, screw 341 contacts an extreme lateral end 351 of the edge of recess 349, additional lateral displacement of anterior portion 266 and posterior portion 276 is restricted to prevent an over tension condition. The widthwise dimension of the headpiece is adjusted as described while locking handle 288 is set to the unlocked position. Lateral displacement of anterior portion 266 and posterior portion 276 is prevented when locking handle 288 is set to the locked position as illustrated.

A padding layer may be attached to secondary housing member 293 to prevent any discomfort resulting from contact with screw 341 or pin 263.

A similarly arranged widthwise displacement limiting unit 365 illustrated in FIG. 24 may be employed when housing member 282A is formed with a plurality of laterally spaced holes 363 sagittally aligned with recess 349 shown in FIG. 23B. A peg 369 is insertable in a selected hole 363 so as to be fixed in place such as being frictionally engaged, and is able to contact an extreme lateral end 351 of the edge of recess 349 to prevent an over tension condition.

FIG. 29A illustrates another embodiment wherein cranial orthosis 610 comprises U-shaped anterior section 205 fitted with widthwise adjustment mechanism 235 as described in relation to FIG. 20 and a posterior section 615, which is configured with a protective layer having an arcuate wide-area occipital piece 635 that may extend to the nape of the neck and integral right and left temple engaging portions 639, and with right and left anteroposterior portions 218 that are able to be coupled with a corresponding anteroposterior portion 208 of anterior section 205 to define a lengthwise adjustment mechanism as described in relation to FIGS. 18A-B. Cranial orthosis 610 also comprises an anterior arcuate securement enhancer 642 engageable with the forehead superior to the forehead engageable member, which is configured with an arcuate inferior portion 647 separably positionable posterior to anterior section 205. Posterior section 615 also comprises an arcuate parietal securement enhancer 652 that may extend to the parietal vertex, which may be releasably attachable to anterior securement enhancer 642 as shown in FIG. 30, such as by hook and loop fasteners. A separate illustration of anterior securement enhancer 642 is shown in FIG. 29B. Anterior securement enhancer 642 and posterior securement enhancer 652 may be padding pieces.

Cranial orthosis 610 may also comprise one or more spacer pads 657, which may be releasably attachable to an orthosis region such as by hook and loop fasteners. If a pad 657 is removed, it may be replaced with a smooth attached surface to avoid irritation to the infant.

FIG. 31 illustrates a posterior pad 657a attached to both occipital piece 635 and parietal securement enhancer 652, and a pad 657b attached to neck piece 633. Anterior securement enhancer 642 and pad 657b are shown in FIG. 32 to be in contact with head 81, to improve securement and to reduce the possibility of unwanted slippage. FIG. 33 illustrates pad 657c attached to anterior securement enhancer 642, for use in pressing on, and treating, a protruding skull deformity. Pad 657c may be circular, for example having a diameter of 50 mm, and suitable to follow the curvature of securement enhancer 642.

As shown in FIG. 34, pads 657a and 657c may be selectively securable to regions of orthosis 610 that take into account a flattened occipital area 645, thereby enhancing cranial remodelling.

Diagnostic Product

In another embodiment, the headpiece of FIG. 1, FIG. 8, FIG. 14 or any other skull-exposed headpiece functions as a diagnostic and therapeutic product (or apparatus) which is adapted to measure data related to the head orientation and mechanical pressure to which the skull of the infant is exposed. Skull orientation is monitored continuously or periodically for short time intervals. It is not required to monitor the head orientation during the entire treatment period, but only during a predetermined time period (for example, 5-15 min.). Also, the electronic system will be designed to be removed and installed easily from the therapeutic device, as needed.

Such data helps to detect muscle imbalance, torticollis, a head positional preference or any other impairment related to head control and head movements. The diagnostic product may be in addition to the therapeutic product (that is aimed to treat skull deformations) while being provided in the same orthosis, or alternatively may be independent of the therapeutic product. An orientation sensor (described later on) that is capable of diagnosing torticollis, can be an add-on device or a stand-alone device.

Figures 5, 6:
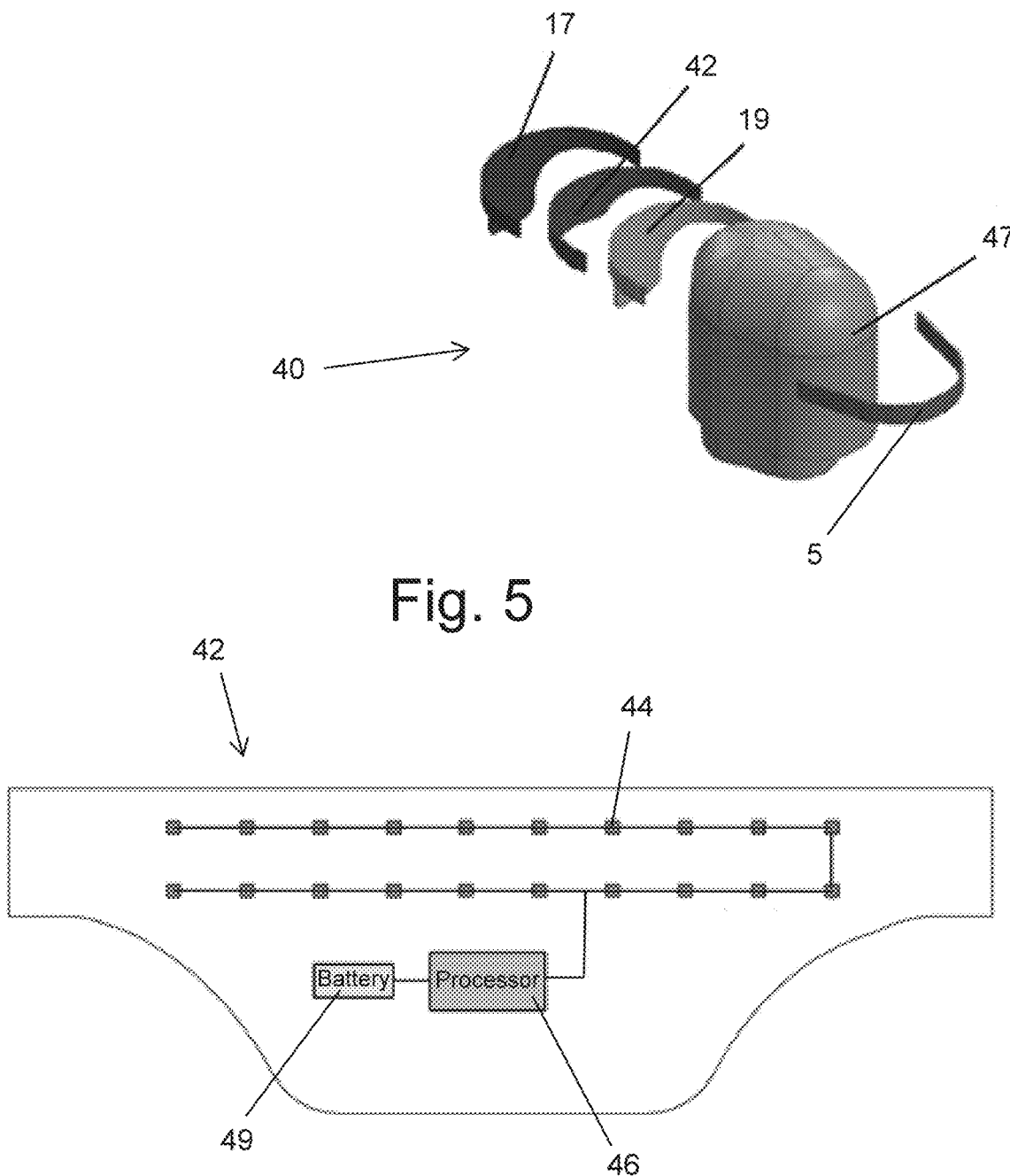
FIG. 5 is an exploded view of an embodiment of a skull securable diagnostic product.
FIG. 6 is a schematic illustration of a sensor module used in conjunction with the diagnostic apparatus of FIG. 5.

FIG. 5 schematically illustrates diagnostic product 40, which comprises one or more sensor modules 42 fitted, for example, between intermediate arcuate piece 17 and padding member 19 and in force transmitting relation therewith (of course, each sensor module 42 may be positioned at a different location along the internal or external surface of the headpiece 10). Sensor module 42 comprising an array of sensors preferably has an arcuate configuration, similar to that of intermediate arcuate piece 17 and padding member 19, and may sagittally protrude from intermediate arcuate piece 17 so as to be additionally in force transmitting relation with one or more of arcuate piece 16 and arcuate piece 18.

Sensor module 42, which may comprise electronic or chemical sensors which are deployed along all regions of contact with the infant's skull, is suitable to continuously measure the mechanical loading on different regions of the skull 47 of a patient secured between the U-shaped anterior section 5 and the posterior section that includes for example arcuate piece 17, and to detect information regarding the amplitude, distribution and duration of accumulative mechanical pressure at each of these skull regions.

In another embodiment, sensor module 42 may be embedded within one or more of arcuate pieces 16-18.

The shape and mechanical properties of the arcuated pieces 16-17-18 (shown in FIG. 1), as well as 103 and 107 (shown in FIG. 8), enable changing the curvature of the pieces according to the adjusted width of the device. The actuated pieces 16-18 change their curvature due to their flexibility and at the same time, they have sufficient strength in order to maintain their shape under the weight of the infants head and prevent collapse, and hence, allow smooth rolling the infant's head.

Also, adjusting the curvature of the pieces allows accurate fitting of the arcuated pieces 16-17-18 to the size of the infant's head. These features keep the symmetrical gap that faces the flat areas and provide an orthosis that is much more versatile than molding helmets due to a continuous adjustment with fixation capability.

The orthosis provided by the present invention solves the flat head syndrome problem, by mainly supporting the perimeter of the infant's head.

The arcuate shape enables on one hand to facilitate space for symmetrical growth of the skull in the inner side, and on the other hand the outer side of the actuated pieces enable smooth rolling movement of the infant's head on the bed surface, without inhibition.

As shown in FIG. 6, sensor module 42 comprises an array of distributed sensors 44 for detecting the force exerted at a corresponding skull region, a microcontroller or any other type of processor 46 for receiving and processing the data signals derived from each sensor 44, and a battery 49 for powering processor 46 and each sensor 44.

In another embodiment, headpiece 10 of FIG. 1 may be modified so as to be a therapeutic product in addition to the previously described diagnostic product. Following determination that the infant is diagnosed with torticollis, a health practitioner may couple a resistance applying element, such as a rigid patch, to a selected region between two of the arcuate pieces 16-18. The selected region to which a patch is coupled is generally contralaterally located with respect to a cervical muscle found to be weakened. This weakened muscle is consequently forced by the patch to be tensioned until the head achieves a balanced condition.

FIG. 7 illustrates another embodiment, according to which the anterior section 5 (shown in FIG. 1) of the adjustable cranial orthosis 10 comprises a single orientation sensor 71, which is insertable into a mating housing 72. By suitably processing the data signals derived from each sensor 44, the presence of asymmetrical cervical muscles often associated with torticollis is able to be determined, so that a therapeutic treatment for this condition is able to be developed, even prior to manifestation of plagiocephaly. Additionally, analysis of the received signals during the therapeutic treatment (which are monitored for a predetermined period every predetermined time) is able to indicate an improvement of the diagnosed torticollis and a gradual achievement of symmetrical musculature to promote a full range of head motion, even before a change in roundness of the skull is noticeable. Monitoring of the orientation allows improving the decisions regarding the next therapeutic steps to be taken and the determination of the required treatment period.

Housing 72 may be attached to the upper face of the anterior section 5 using a connector, such as a spring-loaded pin (also known as a "pogo pin"). Orientation sensor 71 may comprise an electronic module with a gyroscope and/or a 3-D accelerometer, memory and operating software that continuously or periodically measures and records the instantaneous orientation of the infant's head while lying on his back or stomach, or positioned in a sitting or standing position, as well as changes in the orientation over time. The electronic module may facilitate determining the percentage of time relative to the total measuring time that the infant was in each position. The recorded data may be transmitted to a remote server and stored on that server or uploaded for storage in a computational cloud. The stored data may be used later for clinical and research purposes.

The adjustable cranial orthosis 10 may also comprise one or more arched pressure gauge sensors 35, or any other types of force or strain sensor, which measure and record the pressure applied to the infant's head over time. A pressure sensor is well known to those skilled in the art, and therefore need not be described for purposes of brevity. If so desired, the pressure sensor may be in contact with a silicon nipple which is suitable to focus applied pressure from a defined area onto the sensor. A microcontroller or any other type of processor is added and used for processing the recorded data regarding the applied pressure. The measured data may be transmitted to the orientation sensor 71 via a wired connection 74, for storage and transmission to the remote server or to the computational cloud.

According to another embodiment, the orientation sensor 71 is adapted to perform early diagnosis of torticollis and to assist the treatment of torticollis. This is done by monitoring and reporting data regarding the spatial orientation of the infant's head with respect to his body and the surrounding environment. As referred to herein, a "spatial orientation" includes indications regarding roll, pitch and yaw movements of the head. This way, it will be possible to put the adjustable cranial orthosis device 10 (which functions as a diagnostic apparatus) on the infant's head for a predetermined (short) time (e.g., for few minutes) and collect the data. Then, the collected data is stored and analysed, so as to visually illustrate the results to parents and the medical team.

According to another embodiment, a pressure sensor may be inserted into the mating housing 72. The pressure sensor may comprise for example, a strain gauge or a piezoelectric transducer, and is adapted to monitor and report data regarding the magnitude of forces that are exerted at different skull regions as a function of time. Then, the collected data is stored and analysed, so as to visually illustrate the results to the medical team. Measuring the magnitude of forces that are exerted at different skull regions increase the safety while using the cranial orthosis 10 and prevents exceeding the maximum allowable forces (as defined by health authorities).

In another embodiment illustrated in FIGS. 25A-D, diagnostic product 440 is a cranial orthosis that comprises an adjustable headpiece having posterior section 430 configured with a rounded wide-area occipital member 435 that may cover arcuate pieces 196-198 (FIG. 14) as well as with any right and left anteroposterior portions described herein, and an anterior section 410 coupled with posterior section 430 which may be configured similarly to any anterior section described herein. Occipital member 435 may be provided with a parietal region 437 that may extend to the parietal vertex and with an occipital region 438 that may extend to the nape of the neck. In this embodiment, anterior section 410 and posterior section 430 are additionally provided with a protective sheath made for example from textile material with which electronic components of the diagnostic product are integrated.

Electrically interconnected first PCB housing 431 comprising a microcontroller and second PCB housing 432 comprising a battery, such as a replaceable battery, e.g. CR2032, may be attached to parietal region 437. A plurality of pressure sensors 452, e.g. 10-16 sensors, may be attached to occipital region 438 and to anterior section 410 and electrically connected to the microcontroller, and may be addressable. An orientation sensor 454 may be mounted on the forehead engageable member and electrically connected to the microcontroller. Orientation sensor 454 may be an inertial measurement unit (IMU) that comprises at least one accelerometer, and transmits sensed data to the microcontroller. Alternatively, an IMU provided with an orientation sensor 454 comprises at least one accelerometer and at least one gyroscope.

As shown in FIG. 26A, electric connectors 457 are used to connect a wire 453 extending within anterior section 410 to a wire extending within posterior section 430 and to thereby disconnect the wires when anterior section 410 and posterior section 430 are separated for purposes of adjustment.

The structure of a protective sheath 464 provided in posterior section 430 for a plurality of pressure sensors 452 is illustrated in FIG. 26B. Protective sheath 464 has an inner cover 466 contactable with the infant's skull 81 and an outer cover 468 to define a cavity within which the pressure sensors 452 are introduced. The pressure sensors 452 are introduced in a first layer that includes a piece of foam padding 461 extending between two adjacent pressure sensors that are adapted to contact inner cover 466 and to thereby be in sensing relation with the muscles associated with skull 81. A second layer interposed between the first layer and outer cover 468 includes a plurality of rigid elements 469 and foam padding pieces 461 dimensioned to ensure that each rigid element 469 is in abutting relation with a corresponding pressure sensor 452.

The structure of a protective sheath 474 provided in anterior section 410 for one or more pressure sensors 452 is illustrated in FIG. 26C. Protective sheath 474 within which a pressure sensor 452 and foam padding 461 complex is embedded is attached to the posterior face of rigid forehead engageable member 479 comprising the widthwise adjustment mechanism, for example to secondary housing member 293 of FIG. 23A, and is contactable with the forehead of skull 81.

The orthosis has various unique capabilities by being provided with both an orientation sensor and a plurality of pressure sensors that are each of a different spatial orientation. For example, the microcontroller can determine if one or more of the anteroposterior portions or of the posterior arcuate pieces is not adequately secured to the skull when the sensed pressure is less than a predetermined threshold, whereupon a caregiver or health practitioner is alerted to increase the clamping force.

Also as illustrated in FIG. 28A, the microcontroller is configured to determine continuously or periodically the instantaneous orientation 537 of the infant's head, which is acquired from the orientation sensor, relative to the downward extending gravity vector 539, which is acquired from the IMU, regardless of whether the infant is in a supine position, sitting position, standing position such as when being held by a caregiver, or an inclined position. A sitting or standing position is determined when none of the pressure sensors outputs sensed data. A supine position is determined when at least one of the pressure sensors that is contacted by the underlying surface outputs sensed data, and the instantaneous orientation 537 of the infant's head is determined relative to the centerline 541 of the infant at a head joint, such as at the atlanto-occipital joint, whereupon the gravity vector is shifted 90 degrees, as illustrated in FIG. 28B. The microcontroller is also configured to continuously or periodically calculate the pitch, roll and yaw of the infant's head, for example when the infant is sleeping, to determine various head deformities. If the acquired data consistently repeats itself during a given time window, indicating that data related to the gravity vector is constant, the acquired data may be taken into consideration even if the body of the infant accelerates during a movement when data is acquired. In this fashion, the head orientation may be determined with only one IMU.

Additionally, as illustrated in FIG. 27, the microcontroller can determine the oblique head position of a resting infant suffering from a skull deformity, and the orthosis can subsequently be manipulated to correct this condition.

Firstly, the headpiece is secured to the infant's head in step 501 while ensuring that the member to which the orientation sensor is mounted is engaged and in pressure sensing relation with the forehead, whether directly or indirectly such as by means of a piece of padding, and one of the plurality of identical pressure sensors that are interspersed throughout the headpiece is aligned with the forehead engaging member having a planar forehead engaging surface (hereinafter the "aligning sensor"). The microcontroller identifies and receives sensed data from the orientation sensor and all of the pressure sensors in step 503. A calibration operation is then performed in step 505 whereby the subject infant wearing the headpiece is lying in a supine position and a caregiver positions the infant's head until the microcontroller determines that the aligning sensor senses data representative of the highest pressure resulting from contact between the infant's head and the underlying surface (hereinafter "highest contact pressure"). Afterwards, the microcontroller generates a vertical reference line from the aligning sensor that coincides with the planar forehead engaging surface and is perpendicular thereto. The reference line is then stored in memory.

The microcontroller continuously or periodically acquires data representative of the current head position from the orientation sensor in step 507. The microcontroller generates an alert in step 509 if a portion of the headpiece is not adequately secured to the skull when a pressure sensor attached to that headpiece portion, or to a portion proximate thereto, senses a pressure less than a predetermined threshold. A verification operation is occasionally performed in step 511 whereby the subject infant is held in the supine position that generates the reference line and the microcontroller determines whether the aligning sensor senses the highest contact pressure. If another pressure sensor senses the highest contact pressure, the headpiece is readjusted in step 513 and the verification operation is repeated until it is determined that the aligning sensor senses the highest contact pressure. Verified head position data is stored in memory in step 515.

The microcontroller outputs data representative of most frequent head positions in step 517 after having determined the percentage of time relative to the total measuring time that the infant was in each position. A health practitioner relies on the output data to recommend how the headpiece should be readjusted in step 519 to assist in correcting the skull deformity. Alternatively, the microcontroller outputs a recommendation concerning a headpiece adjustment operation.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. An adjustable cranial orthosis configured to induce cranial remodeling to achieve skull symmetry and desired proportions for infants suffering from positional skull deformities, comprising a headpiece capable of encircling, and being secured to, a skull of an infant suffering from positional plagiocephaly, brachycephaly or scaphocephaly in such a way that contact between a flattened occipital area of the infant and a flat surface on top of which the infant is lying is prevented so that unrestricted occipital growth is able to be induced, and is such a way that the headpiece gently restricts the growth of a head in prominent areas, wherein said headpiece comprises separate posterior and anterior sections that are capable of being coupled together, a widthwise adjustment mechanism operatively connected to the anterior section, and at least one lengthwise adjustment mechanism operatively connected to the posterior section, and wherein the widthwise adjustment mechanism and the at least one lengthwise adjustment mechanism are operable to suitably adjust the headpiece to take into account cranial growth of the infant and to redirect the head growth, wherein the anterior section is U-shaped and is configured with at least two spaced anteroposterior portions and a forehead engageable member which is provided with the widthwise adjustment mechanism, and the posterior section is U-shaped and is configured with two spaced anteroposterior portions, and wherein each of the anteroposterior portions of the anterior section is adjustably and releasably coupled with a corresponding anteroposterior portion of the posterior section with one of the lengthwise adjustment mechanisms, wherein the anterior section comprises two L-shaped elements each of which provided with one of the anteroposterior portions and a planar laterally extending element, and wherein the widthwise adjustment mechanism is configured to simultaneously displace the two laterally extending elements, and wherein each of the two laterally extending elements is formed with a corresponding groove, and the forehead engageable member is integrally formed with an insert from which a fixation element connected thereto extends through the corresponding groove formed in each of the laterally extending elements, thereby facilitating widthwise adjustment of the orthosis upon displacement of a first of the laterally extending elements relative to a second of the laterally extending elements and upon securing said fixation element.

2. The adjustable cranial orthosis according to claim 1, wherein the posterior and anterior sections are semi rigid, flexible or rigid.

3. The adjustable cranial orthosis according to claim 1, wherein the posterior section is configured with one or more arcuate pieces that follow a contour of a symmetric skull.

4. The adjustable cranial orthosis according to claim 3, wherein the headpiece further comprises a curved brace inserted within, and attached to, a corresponding arcuate piece, said curved brace being pivotally connected by a transversal pivot to a protruding portion of an appendage fixedly attached to an insert to facilitate angular adjustment of the corresponding arcuate piece about a lateral axis.

5. The adjustable cranial orthosis according to claim 3, wherein the headpiece further comprises a padding member attached to an inner face of the one or more arcuate pieces, allowing the infant's head to rest in a concave space defined by the one or more arcuate pieces and the padding member until a rounded cranium structure is achieved.

6. The adjustable cranial orthosis according to claim 5, wherein the headpiece further comprises a sensor module fitted between at least one of the arcuate pieces and the padding member or at different locations along an internal or external surface of the headpiece and in force transmitting relation therewith, to continuously measure data related to mechanical pressure to which the skull of the infant is exposed.

7. The adjustable cranial orthosis according to claim 6, wherein the sensor module comprises an array of distributed sensors for detecting a force exerted at a corresponding skull region, a microcontroller for receiving and processing data signals derived from each of said sensors for measuring said force, and a battery for powering said microcontroller and each of said sensors.

8. The adjustable cranial orthosis according to claim 6, wherein the sensor module has an arcuate configuration.

9. The adjustable cranial orthosis according to claim 5, wherein the padding member has two spaced temple engaging portions and an arcuate occipital portion extending continuously from one temple engaging portion to another and of increased width relative to the two temple engaging portions.

10. The adjustable cranial orthosis according to claim 9, wherein one of the temple engaging portions of the padding member is attached to a corresponding anteroposterior portion of the anterior section.

11. The adjustable cranial orthosis according to claim 1, wherein each of the anteroposterior portions of the anterior section is formed with a groove within which an insert extends, thereby facilitating lengthwise adjustment of the orthosis.

12. The adjustable cranial orthosis according to claim 1, wherein each of the at least one lengthwise adjustment mechanism comprises a resilient clamping unit.

13. A diagnostic and therapeutic apparatus for detecting and treating torticollis or cervical muscle imbalance, comprising a headpiece capable of encircling, and being secured to, regions of a subject's head, a microcontroller, and a single orientation sensor exclusively which is mounted on said headpiece and is in data communication with said microcontroller to continuously or periodically measure data related to an instantaneous orientation of the subject's head, as well as changes in said orientation over time, wherein said orientation sensor is an inertial measurement unit (IMU) that comprises at least one accelerometer, wherein said microcontroller is configured to generate a gravity vector from said IMU, to determine the instantaneous orientation of the subject's head relative to the generated gravity vector, and to thereby determine a location of asymmetrical cervical muscles, wherein said headpiece comprises separate posterior and anterior sections that are capable of being coupled together, wherein said headpiece comprises separate posterior and anterior sections that are capable of being coupled together, a widthwise adjustment mechanism operatively connected to the anterior section, and at least one lengthwise adjustment mechanism operatively connected to the posterior section, and wherein the widthwise adjustment mechanism and the at least one lengthwise adjustment mechanism are operable to suitably adjust the headpiece to take into account cranial growth of the subject and to redirect the head growth, wherein the anterior section is U-shaped and is configured with at least two spaced anteroposterior portions and a forehead engageable member which is provided with the widthwise adjustment mechanism, and the posterior section is U-shaped and is configured with two spaced anteroposterior portions, and wherein each of the anteroposterior portions of the anterior section is adjustably and releasably coupled with a corresponding anteroposterior portion of the posterior section with one of the lengthwise adjustment mechanisms, wherein the anterior section comprises two L-shaped elements each of which provided with one of the anteroposterior portions and a planar laterally extending element, and wherein the widthwise adjustment mechanism is configured to simultaneously displace the two laterally extending elements, and wherein each of the two laterally extending elements is formed with a corresponding groove, and the forehead engageable member is integrally formed with an insert from which a fixation element connected thereto extends through the corresponding groove formed in each of the laterally extending elements, thereby facilitating widthwise adjustment of the apparatus upon displacement of a first of the laterally extending elements relative to a second of the laterally extending elements and upon securing said fixation element.

14. The diagnostic and therapeutic apparatus according to claim 13, further comprising an array of distributed pressure sensors in data communication with the microcontroller which are mounted on the headpiece, for detecting a force exerted at a corresponding head region, wherein the microcontroller is configured to determine that the subject is in a lying position when at least one of the pressure sensors outputs data signals and to angularly shift the generated gravity vector by 90 degrees.

15. The diagnostic and therapeutic apparatus according to claim 14, wherein each of the pressure sensors is arched.

16. The diagnostic and therapeutic apparatus according to claim 13, further comprising a resistance applying element coupled to a selected region of a posterior section of the headpiece which is contralaterally located with respect to the determined location of asymmetrical cervical muscles, said resistance applying element configured to induce tensioning of the asymmetrical cervical muscles until the subject's head achieves a balanced condition.

17. A method for diagnosing a skull deformity or a cervical muscle imbalance, comprising the steps of providing a headpiece to which is mounted a forehead engaging member, a microcontroller, an orientation sensor and a plurality of identical pressure sensors for being positioned at spatially different head locations; securing said headpiece to the head of a subject while ensuring that one of the pressure sensors is aligned with the forehead engaging member; by said microcontroller, identifying and receiving data from said orientation sensor and said plurality of pressure sensors; performing a calibration operation by generating a vertical reference line that extends from the aligning sensor upon determining that the aligning sensor senses a highest contact pressure among all of the plurality of pressure sensors;

acquiring data representative of a current head position relative to the reference line from the orientation sensor; verifying the acquired head position by determining whether the aligning sensor senses the highest contact pressure; readjusting said headpiece until the aligning sensor senses the highest contact pressure; storing the verified head position data; and outputting data representative of most frequent head positions, wherein said headpiece comprises separate posterior and anterior sections that are capable of being coupled together, wherein said headpiece comprises separate posterior and anterior sections that are capable of being coupled together, a widthwise adjustment mechanism operatively connected to the anterior section, and at least one lengthwise adjustment mechanism operatively connected to the posterior section, and wherein the widthwise adjustment mechanism and the at least one lengthwise adjustment mechanism are operable to suitably adjust the headpiece to take into account cranial growth of the subject and to redirect the head growth, wherein the anterior section is U-shaped and is configured with at least two spaced anteroposterior portions and a forehead engageable member which is provided with the widthwise adjustment mechanism, and the posterior section is U-shaped and is configured with two spaced anteroposterior portions, and wherein each of the anteroposterior portions of the anterior section is adjustably and releasably coupled with a corresponding anteroposterior portion of the posterior section with one of the lengthwise adjustment mechanisms, wherein the anterior section comprises two L-shaped elements each of which provided with one of the anteroposterior portions and a planar laterally extending element, and wherein the widthwise adjustment mechanism is configured to simultaneously displace the two laterally extending elements, and wherein each of the two laterally extending elements is formed with a corresponding groove, and the forehead engageable member is integrally formed with an insert from which a fixation element connected thereto extends through the corresponding groove formed in each of the laterally extending elements, thereby facilitating widthwise adjustment of the headpiece upon displacement of a first of the laterally extending elements relative to a second of the laterally extending elements and upon securing said fixation element.

* * * * *